US006532383B2

United States Patent
Maloney et al.

(10) Patent No.: US 6,532,383 B2
(45) Date of Patent: Mar. 11, 2003

(54) APPARATUS AND METHODS FOR DETECTING AND PROCESSING EMG SIGNALS

(76) Inventors: Sean R. Maloney, 405 Sondley Woods Place, Asheville, NC (US) 28805; Sarah C. Shoaf, 1122 W. Fourth St., Winston-Salem, NC (US) 27101; Ian M. Zlotolow, 402 E. 64th St., Apt. 4e, New York, NY (US) 10021-7826

( * ) Notice: Subject to any disclaimer, the term of this patent is extended or adjusted under 35 U.S.C. 154(b) by 126 days.

(21) Appl. No.: 09/791,459

(22) Filed: Feb. 23, 2001

(65) Prior Publication Data

US 2001/0025146 A1 Sep. 27, 2001

Related U.S. Application Data

(62) Division of application No. 09/267,301, filed on Mar. 15, 1999, now Pat. No. 6,280,394.
(60) Provisional application No. 60/078,466, filed on Mar. 18, 1998.

(51) Int. Cl.$^7$ ................................................. A61B 5/04
(52) U.S. Cl. ....................................... 600/546; 600/540
(58) Field of Search ................................. 600/529–547, 600/587–595

(56) References Cited

U.S. PATENT DOCUMENTS

| | | | |
|---|---|---|---|
| 4,334,542 A | 6/1982 | Takinishi et al. | 600/395 |
| 4,355,645 A | 10/1982 | Mitani et al. | 600/590 |
| 4,605,927 A | 8/1986 | Katz et al. | 340/825.19 |
| 5,212,476 A | 5/1993 | Maloney | 340/825.19 |
| 5,523,745 A | 6/1996 | Fortune et al. | 340/825.19 |
| 5,689,246 A | 11/1997 | Dordick et al. | 340/825.19 |

*Primary Examiner*—Max F. Hindenburg
*Assistant Examiner*—Pamela L. Wingood
(74) *Attorney, Agent, or Firm*—Carter & Schnedler, P.A.

(57) ABSTRACT

Methods are provided for smoothing input signals having rapidly changing amplitudes, such as EMG signals from the tongue, which are detected by an intraoral device. One method calls for amplifying the EMG signals, converting the EMG signals to digital format, providing a moving average of the amplitudes of the EMG signals utilizing a moving the average processor, and windowing the averaged signals to discrete and stable amplitude levels. An adaptive moving average technique may be utilized, which includes a plurality of parallel moving average processes and a differentiator which determines which process is used, depending on the rate of change of the signal amplitude. Another method calls for the use of a plurality of moving average processes in series which calculate the moving average of the same number of signals as a single moving average process, but has a faster response time. An intraoral device is used to detect the EMG signals. The intraoral device includes acrylic maxillary and mandibular splints. The maxillary splint has reference electrodes attached to its palate side, while the mandibular splint has active electrodes attached to the gum side. The intraoral device is strengthened by the use of woven fiberglass imbedded in its acrylic body.

3 Claims, 24 Drawing Sheets

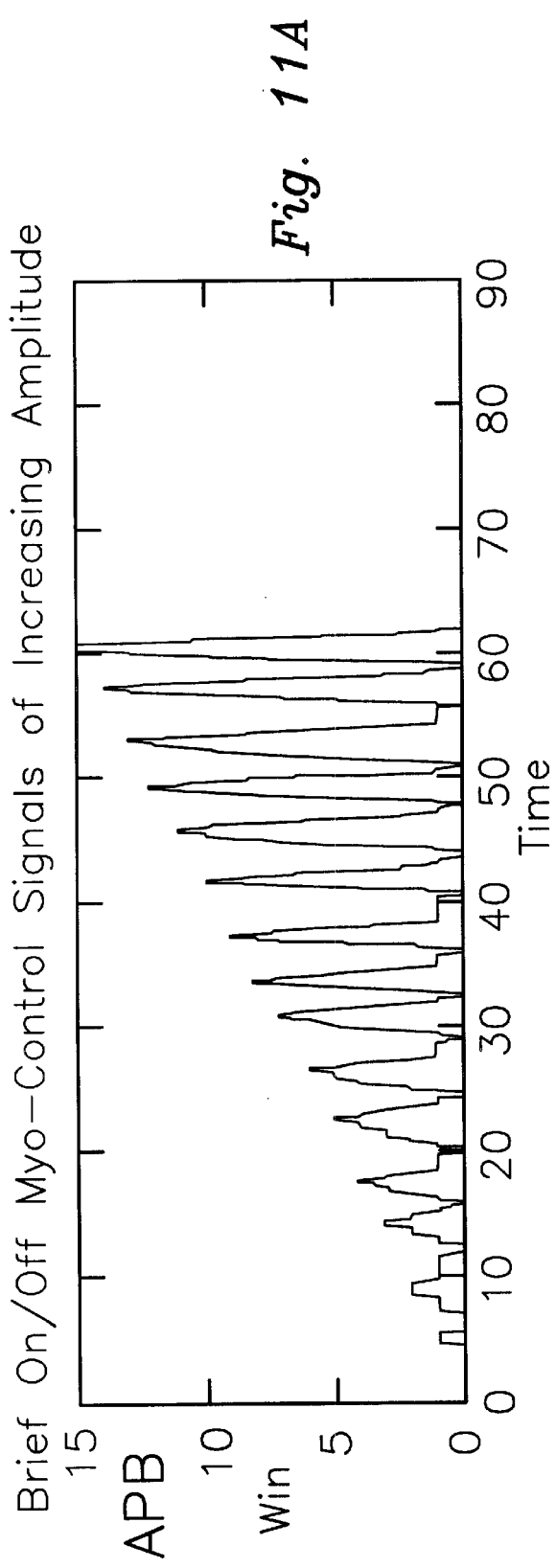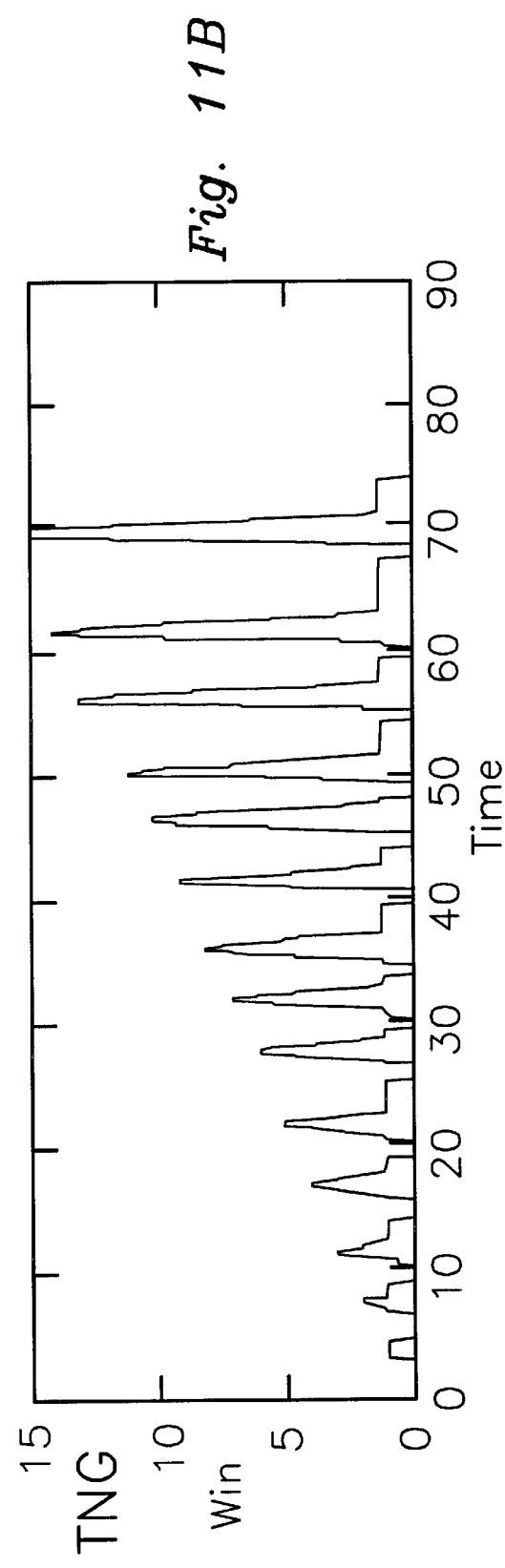

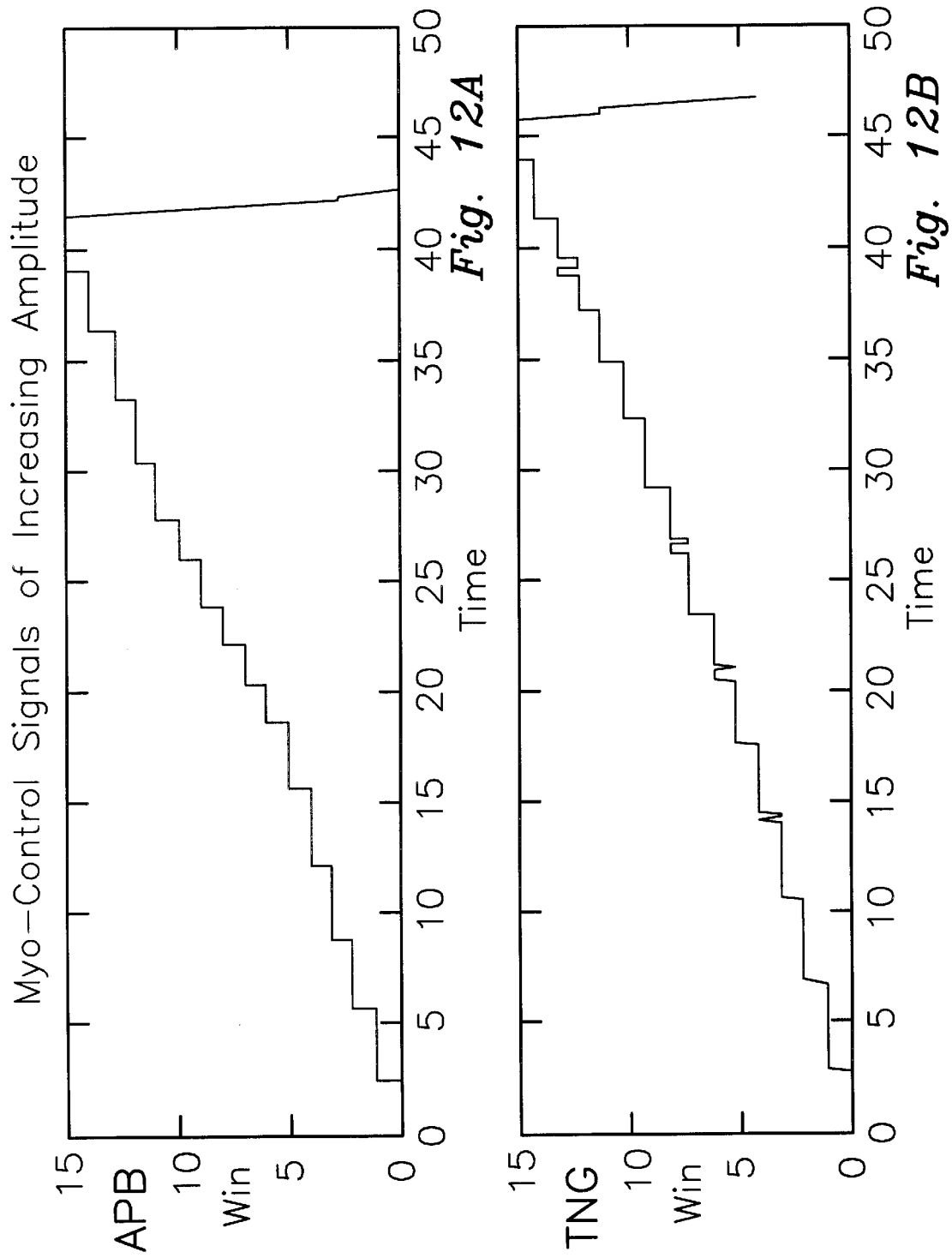

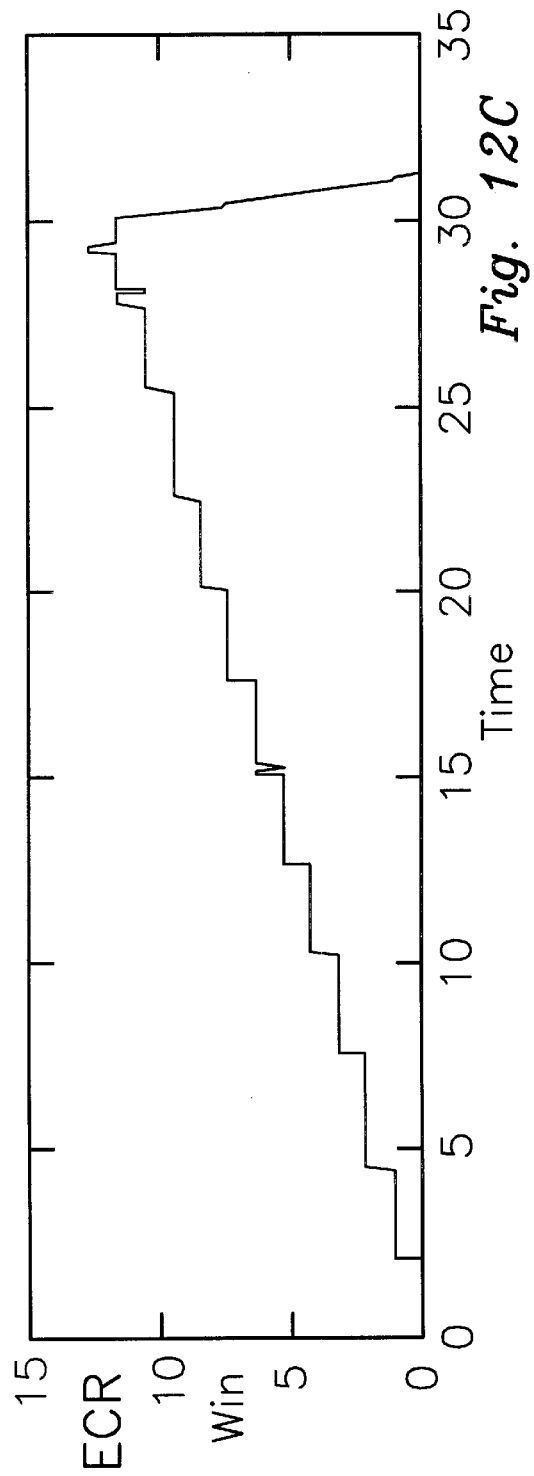
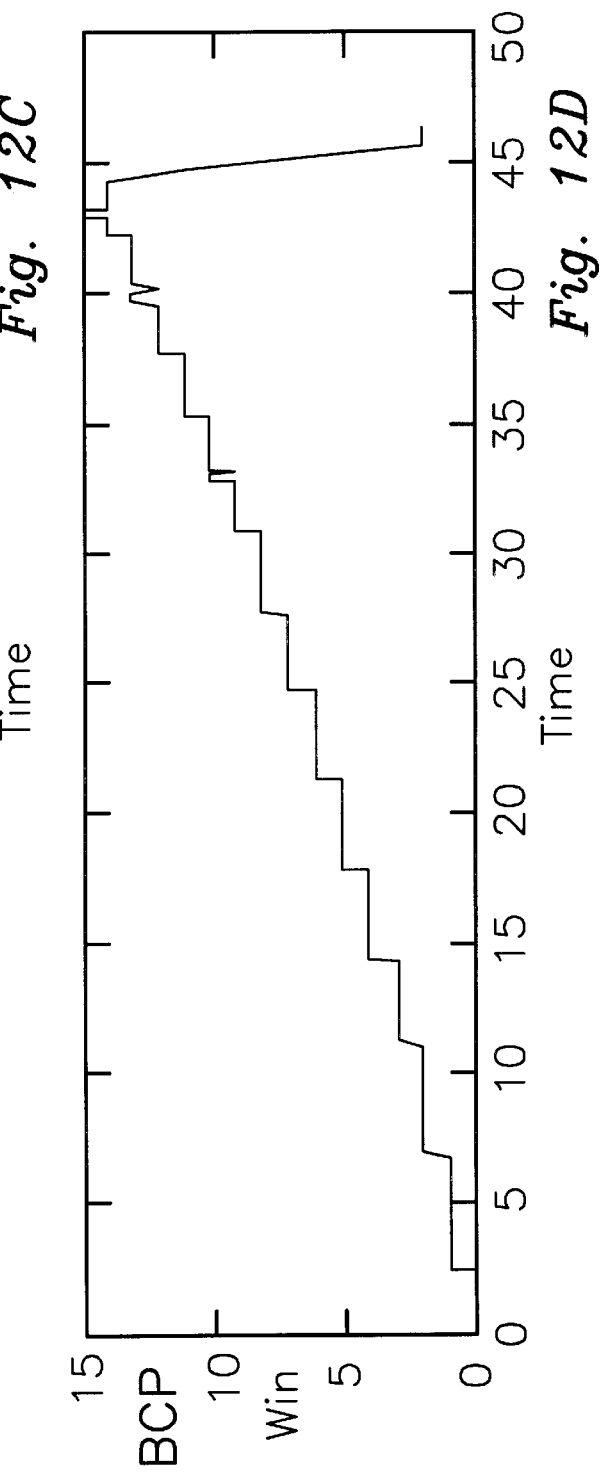
Fig. 12C
Fig. 12D

ECR Myoelectric Control Signal as a
Step Function of 16 Levels

ECR Myoelectric Control Signal Held at
the 2,6,10,& 14 Levels for About 30 Sec.

Brief On/Off ECR Myoelectris Control Signal of Increasing Amplitude Over 16 Levels BCP Myoelectric Control Signal as a Step Function of 16 Levels BCP Myoelectric Control Signal Held at the 2,6,10,& 14 Levels for About 30 Sec.

Brief On/Off BCD Myoelectris Control Signal of Increasing Amplitude Over 16 Levels

32 Level APB Myoelectric Control Tasks

APB Myoelectric Control Signal as a
Step Function of 32 Levels

APB Myoelectric Control Signal Held at
the 4, 12, 20, & 28 Levels for About 30 Sec.

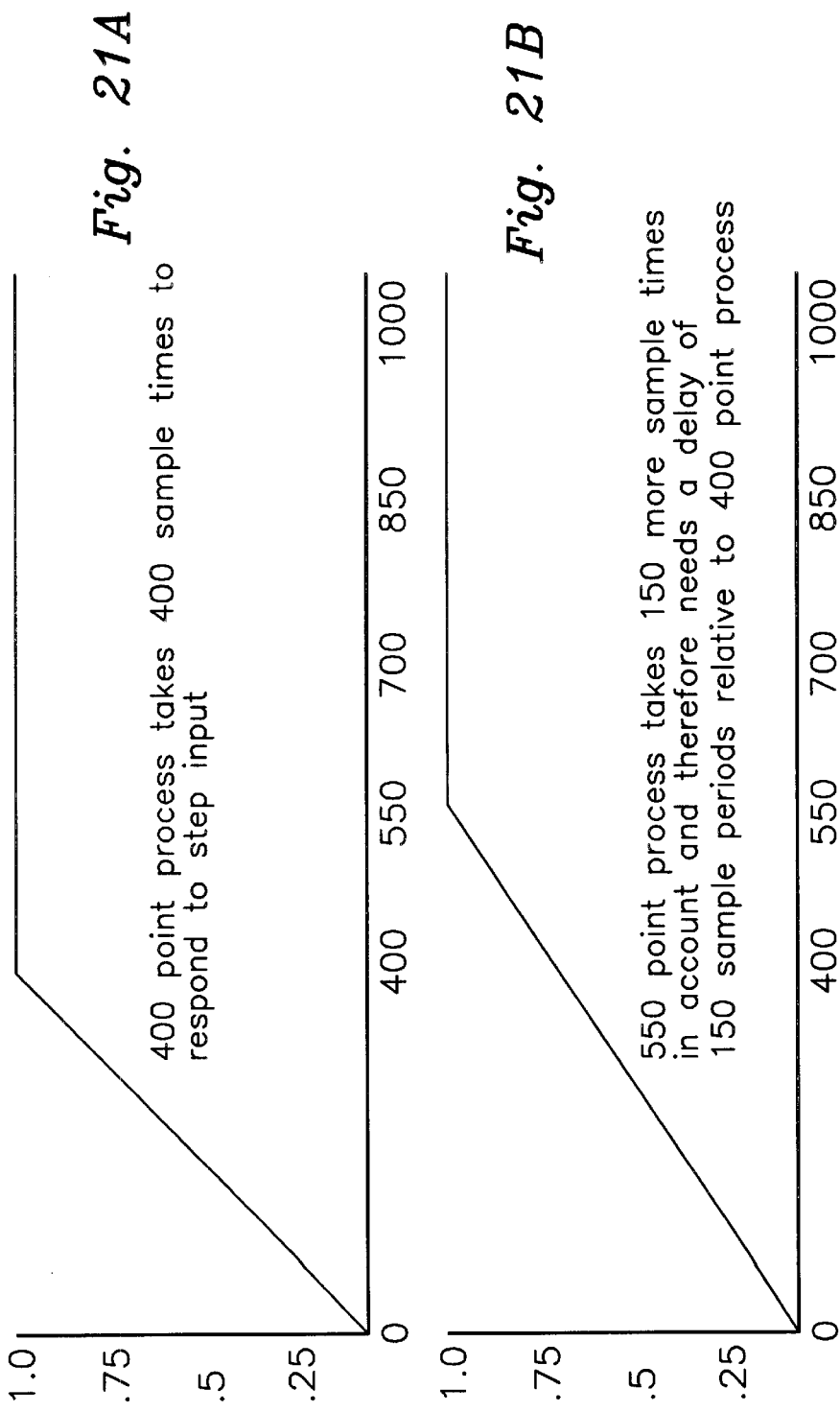

APPARATUS AND METHODS FOR DETECTING AND PROCESSING EMG SIGNALS

CROSS-REFERENCE TO PROVISIONAL PATENT APPLICATION

This application is a division of application Ser. No. 09/267,301, filed Mar. 15, 1999, now U.S. Pat. No. 6,280,394, which claims the benefit of U.S. Provisional patent application Ser. No. 60/078,466, filed Mar. 18, 1998, is claimed.

U.S. GOVERNMENT RIGHTS

This invention was made with government support under Grant Nos. R43-NS31074-01 and R44-NS31074-02A1 awarded by the National Institutes of Health. The government has certain rights in the invention.

BACKGROUND OF THE INVENTION

This invention relates to the detection and processing of rapidly changing bioelectric or other signals. More particularly, it relates to methods for detecting, processing smoothing signals having rapidly changing amplitudes, such as EMG signals, which may be generated by the tongue or other muscles, and for providing stable and discrete output signals from input signals detected by a detector, such as an intraoral device.

The use of electromyographic (EMG) signals for control of a prosthesis was proposed by Reiter in 1948. In 1958, an actual surface EMG or myoelectrically controlled prosthetic hand was introduced in Russia. EMG signals recorded from remaining agonist and antagonist muscles in the residual limb of a transradial amputee were used. Since the 1960's, the use of myoelectric control of prostheses and orthoses has continued to be studied and successfully implemented. There are now myoelectric prosthetic devices which use surface EMG signals recorded from one or two muscle sites for proportional or digital actuation of one or more functions of an electric powered prosthetic component.

During the late 1960's and early 1970's, electromyographic or myoelectric based control strategies were studied and compared with myomechanical position controllers. The use of surface EMG or myoelectric controllers has been limited by the long integration intervals required to stabilize rapidly fluctuating surface EMG signals. These long integration intervals slow down the responsivity of the controller. A second limitation of myoelectric controllers has been the small number of resolvable discrete control signal levels obtainable (approximately five). Myomechanical position controlling systems have been found to provide a greater number of discrete control levels, as well as more stable control signals.

A myomechanical technique has been developed for use with mid-cervical spinal cord injured individuals using shoulder movement transduction for proportional two-axis control of prosthetic and orthotic systems, including systems employing functional electrical stimulation. Limitations in using shoulder movement transduction for proportional two-axis control of orthotic and neuroprosthetic systems in the high quadriplegic include a) a decrease in the number of discrete control signal levels achievable and a decrease in the stability of the control signals as the level of spinal cord injury become higher, b) control signal interference from motion of the contralateral shoulder, c) instability of reference position due to postural changes and attachment methods of the position transduce, and d) difficulty in concealing the transducer. Recently there has been renewed interest in using processed surface EMG or myoelectric signals as control signals in spinal cord injured individuals in a single dimensional functional electrical stimulation task.

Oral motor and sensory impairments, including dysphagia and dysarthria, can result from many causes including: traumatic brain injury, cerebral palsy, stroke and other diseases of the nervous system such as Parkinson's disease, multiple sclerosis and amyotrophic lateral sclerosis. The occurrence of oral motor and sensory dysfunction increases with age and can result in increased difficulty with communication, decline in nutritional status and, in some cases, aspiration pneumonia. Improved methods for measuring intraoral motor and sensory function are needed.

Electromyographic (EMG) signals from the genioglossus muscle have been previously measured using surface electrodes placed over the skin under the mandible and using surface electrodes mounted to mandibular appliances or splints. With previous intraoral EMG recording techniques, two to four electrodes are used. Electrode wires exit the mouth anteriorly between the upper and lower incisors and hinder approximation of the teeth.

The mounting of two surface electrodes 3 mm in diameter to the palate side of a maxillary splint has been described by Schwarts, et al. Used to stimulate the soft palate, these electrodes were located 1 cm apart, centered to midline, and 2–3 cm posterior to the vibrating line on the soft palate. The methods by which the two electrode wires exited the mouth was not described.

U.S. Pat. No. 5,212,476 invented by Sean R. Maloney describes an intraoral device for detecting EMG signals from the tongue. The Maloney device describes a single splint having a convex side which may be in contact with either the maxillary or mandibular and includes active electrodes mounted on the splint adjacent to the tongue.

OBJECTS OF THE INVENTION

It is therefore one object of the invention to provide an improved method for smoothing input signals having rapidly changing amplitudes.

It is another object of the invention to provide an improved method for converting EMG signals generated from the tongue to signals having stable and discrete levels.

It is still another object of the invention to provide an improved intraoral device for detecting EMG signals from the tongue.

SUMMARY OF THE INVENTION

One aspect of this invention calls for digital processing techniques which can smooth and stabilize a bioelectric of other signal amplitude and an integrated (with respect to time) bioelectric or other integrated signal amplitude which change rapidly in an irregular or random (stochastic) fashion due to the asynchronous nature of the constituent or contributing components of the signal or integrated signal amplitude. The fluctuatory signal amplitude to be processed can be a unipolar (+ or −) or a bipolar (+ and −) signal amplitude. Examples of bipolar bioelectric signal amplitudes which can be processed using the techniques include electromyographic (EMG) or myoelectric, electroneurographic (ENG) or nerve, and electroencephalographic (EEG) or brain signal amplitudes.

These signal processing techniques decrease signal or integrated signal amplitude variability (i.e., smooth the signal or integrated signal amplitude) using an adaptive moving average process and an exponential average process while maintaining signal or integrated signal amplitude responsiveness (i.e., adequate rate of signal or integrated signal amplitude change for a given application). The signal or integrated signal amplitude is stabilized by converting the smoothed but still fluctuating signal or integrated signal amplitude into a discrete signal, or integrated signal, amplitude using an interactive variable windowing process. Smoothing the varying signal or integrated signal amplitude prior to forming a discrete or stable signal or integrated signal amplitude increases the number of resolvable signal or integrated signal amplitude values. Using this signal or integrated signal amplitude stabilizing technique allows the discrete signal or integrated signal value to be maintained for a time interval suitable for the digital signal processing application.

One potential application for these digital signal processing techniques is the conversion of a fluctuating surface electromyographic (EMG) signal amplitude or integrated surface EMG signal amplitude into a processed myoelectric, signal or integrated signal, amplitude to control orthotic (brace), prosthetic (artificial limb), neuroprosthetic (prosthesis which uses limb functional electrical stimulation), robotics, and other (external) devices.

A second application for these digital signal processing techniques is the conversion of a bioelectric or other randomly changing signal, or integrated signal, amplitude into a series of discrete signal amplitudes or discrete integrated signal amplitudes for signal or integrated signal amplitude measurement purposes. These techniques allow resolution of the processed signal amplitude or integrated signal amplitude into discrete time and discrete signal amplitude or integrated signal amplitude domains. For example, rectified EMG or integrated EMG signal amplitudes could be processed into smoothed and stabilized discrete amplitude or integrated amplitude values. These discrete values could then be plotted as a function of time or sorted by discrete signal value for a given length of time and plotted as a histogram.

In accordance with one form of the invention, there is provided a method for smoothing input signals having rapidly changing amplitudes utilizing an adaptive moving average processor. The method includes the steps of: providing a plurality of parallel moving average processes; each of the moving average processes for averaging a different number of signals; each of the processes receive the input signals; providing a differentiator which receives an average of the signals from one of the processes for determining the rate of change of the signals; and selecting one of the processes for providing an output of the average of the signals based on the rate of change of the signal. The words "moving average process" are used to describe a portion of a computer program which calculates the moving average of the signal or integrated signal amplitudes over a period of time.

In accordance with another form of the invention, there is provided a method for smoothing input signals having rapidly changing amplitudes utilizing a compound moving average processor. The method includes the steps of: providing at least first and second moving average processes in series; providing a rapidly changing input signal to the first process; the averaged output signal from the first process becoming the input signal to the second process, so that the responsiveness of the first and second processors is greater than the responsiveness of a single moving average process which calculates the average of the same number of signal amplitudes as the combination of the first and second processes.

In accordance with another form of the invention, there is provided a method for smoothing input signals having rapidly changing amplitudes utilizing an adaptive moving average processor. The method includes the steps of: calculating the moving average of input signal amplitudes for a first predetermined period of time; calculating the moving average of input signals for a second predetermined period of time which includes the first period of time, whereby more signals are averaged during the second predetermined period of time than the first predetermined period of time; determining the rate of change of the amplitudes of the signals; selecting only one of the calculated averages based on the rate of change of the signal amplitudes; and selecting the second calculated average if the rate of change of the signal amplitude is low.

In accordance with another form of the invention, there is provided a method for smoothing input signals having rapidly changing amplitudes utilizing a compound moving average processor. The method includes the steps of: calculating the moving average value of the amplitude of the input signals, thereby providing a first average of the input signal amplitudes; and calculating the moving average value of the output of the first calculation of moving average, whereby the responsiveness for the first calculation and the second calculation is greater than the responsiveness of a single calculation which calculates the average of the same number of signal amplitudes as the first and second calculations.

In accordance with another form of the invention, there is provided a method for converting EMG signals having rapidly changing amplitudes to signals having stable and discrete levels. The method includes the steps of: detecting EMG signals from electrodes on an intraoral device; amplifying the EMG signals; converting the EMG signals to digital format; providing a moving average of the amplitudes of the EMG signals; and windowing the average signals to discrete and stable amplitude levels.

In accordance with another form of the invention, there is provided an intraoral device for detecting EMG signals from the tongue. The device includes a maxillary splint and a mandibular splint. The maxillary splint has a palate side which is adapted to be in contact with the palate of a patient. The mandibular splint has a gum side which is adapted to be in contact with the gum of the patient. At least one reference electrode is attached to the palate side of the maxillary splint. At least one active electrode is attached to the gum side of the mandibular splint. The reference electrode will make contact with the patient's palate and the active electrode will make contact with the patient's gum so that the detection of EMG signals from the tongue is enhanced.

In accordance with another form of the invention, there is provided an intraoral device for detecting EMG signals from the tongue. The device includes a splint having at least one electrode attached thereto. The splint is made of acrylic. Woven fiberglass is imbedded in the acrylic for increasing the strength of the splint. The woven fiberglass may be twisted near its midpoint.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

FIGS. 12(A–D) show four graphs illustrating myo-control signal steps of increase in amplitudes;

FIGS. 13(D–G) show four graphs of sustained on/off myoelectric control signals at various amplitudes;

DESCRIPTION OF THE PREFERRED EMBODIMENTS

U.S. patent application Ser. No. 5,212,476 teaches techniques for interfacing an intraoral EMG detector with an EMG signal processor and is hereby incorporated herein by reference.

Figure 1A:
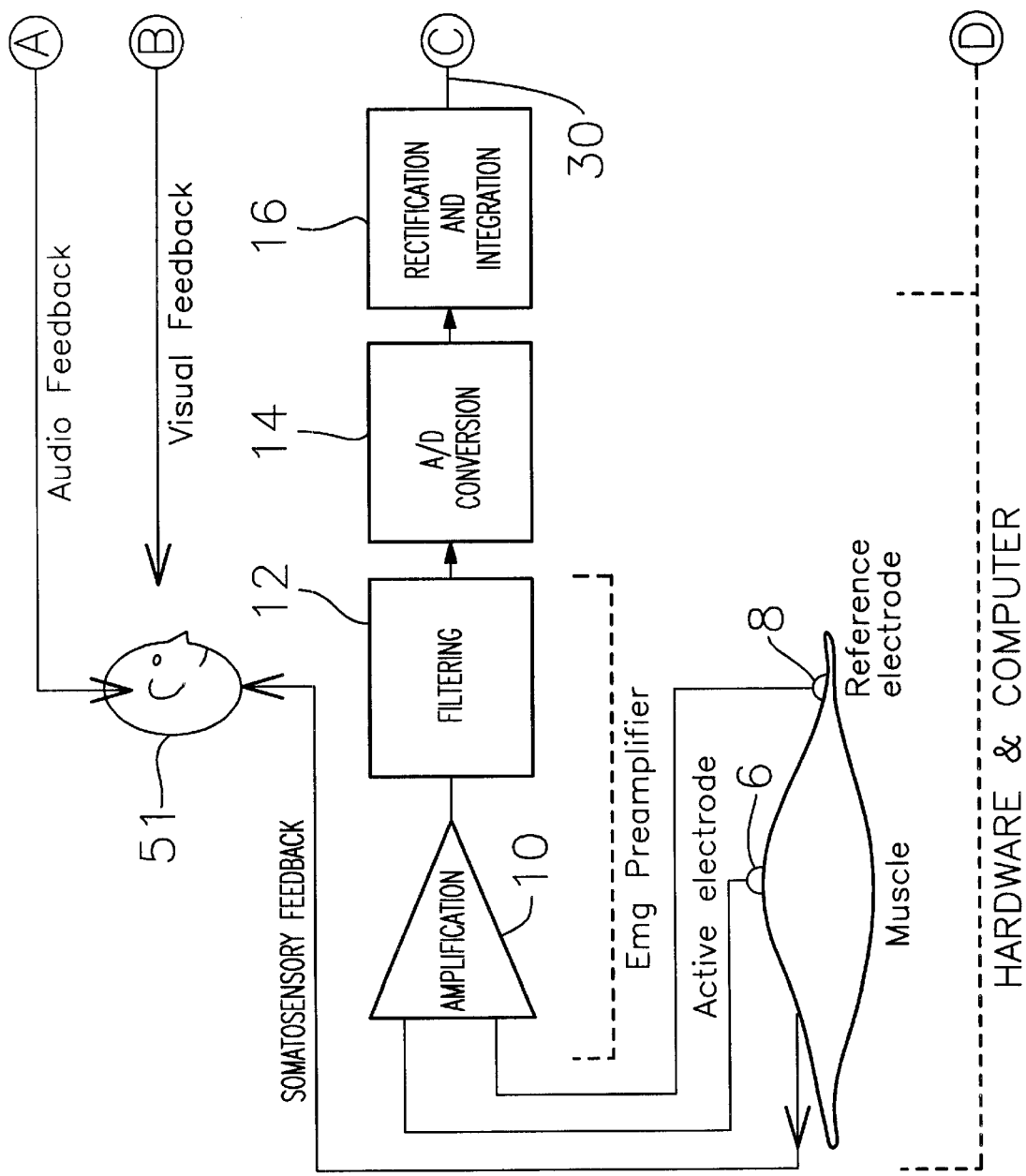
FIGS. 1(A–B) show a schematic diagram showing one embodiment of the signal processing part of this invention.
Figure 1B:
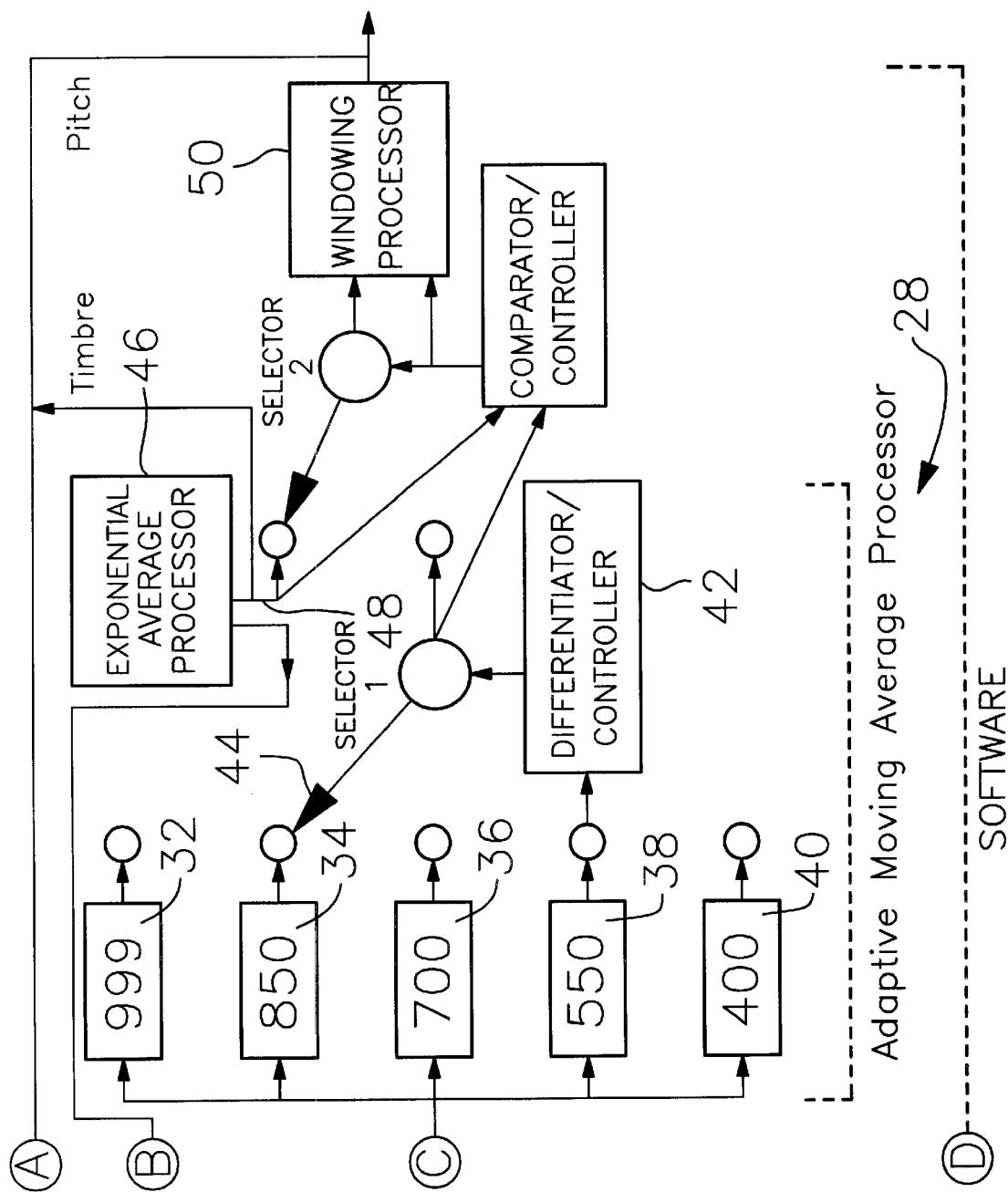
Figure 3:
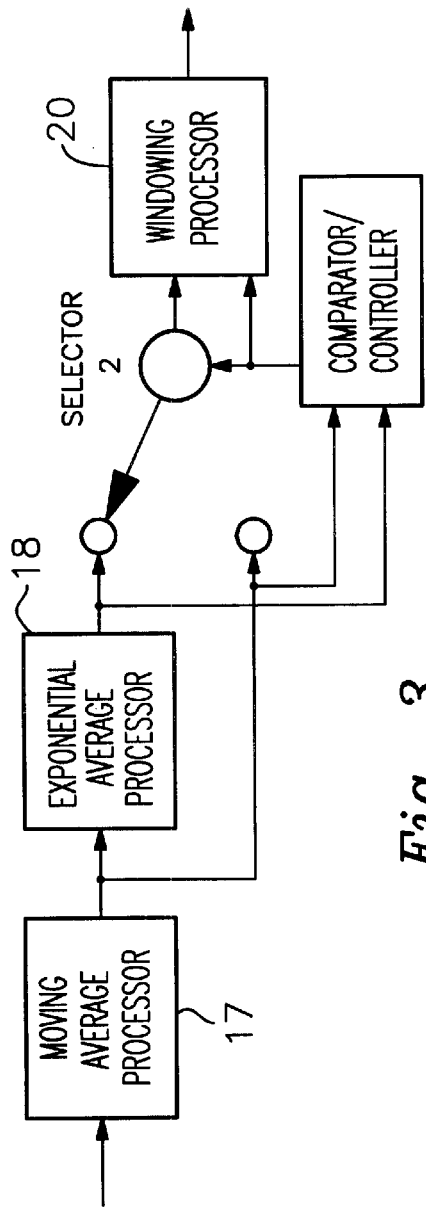
FIG. 3 is a schematic diagram of an alternative embodiment of FIG. 2.

Referring now more particularly to FIGS. 1A–B and 3, single channel EMG signals are recorded by a pair of one centimeter in diameter stainless steel recording disk electrodes 6 and 8. The active electrode 6 is located in proximity to a muscle, such as the tongue, as close to the motor end point as possible, and the reference electrode 8 is located over a muscle tendon or other more signal neutral location, such as the hard palate. The surface recording electrodes and a similar surface ground electrode are then connected to a Grass F-P51C31 patient protect cable. This cable is then connected to a Grass P511 amplifier with built in filters. The P511 amplifier 10 is powered by a Grass RPS212 medical grade power supply.

The EMG signal amplified by amplifier 10 is conditioned by a high pass 30 Hz filter, a low pass 10 KHz filter, and a 60 cycle notch filter designated as filter 12. The filtered EMG signal is then connected to a Keithley Metrobyte DAS-1602 data acquisition board in a P.C. with an Intel 266 MHz Pentium II CPU. The entire system is connected to 60 Hz, 120V line current through a Magnetek Triad Model N-92MD™ medical grade isolation transformer.

A four-channel Nicolet Viking IV P® EMG/NCV machine was also connected to our EMG signal processing system (P.C. with A/D board) in order to view and record in real time the actual EMG signals which were being processed into control signals. The Nicolet MMP Software Program® was used to view and record actual EMG signals while the P.C. with A/D board simultaneously processed and recorded the processed EMG signals.

The software illustrated in schematic in FIG. 3 for EMG signal processing was written in Borland C. The program uses both the direct memory access (DMA) capability of the Keithley Metrobyte DAS-1602 analog to digital P.C. conversion board and advanced drivers for this A/D board provided by Keithley Metrobyte. Continuous EMG signal processing is performed and audio/visual feedback provided using an Intel 266 MHz Pentium II central processing unit (CPU). Various stages of the processed EMG signal, including that of the final EMG control or myo-control signals may be stored in files. The data in these files are then plotted and analyzed using Mathcad 4.0™.

EMG signals from each of the four Grass P511 amplifiers are sampled twenty-five thousand times a second using a Keithley Metrobyte A/D converter. The digital signals are then rectified (converted to their absolute values $|a|$), integrated over a 3.2 millisecond interval, and stored in the computers memory. The rectification and integration is illustrated as block 16 in FIGS. 1(A–B).

The initial smoothing of the stored signals is accomplished by a moving average processor 17. The number of moving average processor points that can be used for a given signal integration time is limited by the desired responsiveness of the processed myo-control signal. The number of moving average processor points is adjustable between approximately 400 and 1000. A given signal amplitude integration time interval is limited by the desired responsivity of the processed EMG signal.

A mathematical description of the moving average process value NSUM is set forth below.

Let A=the EMG Signal Value integrated over the time T. Then $$A = \sum_{j=1}^{N} |a_i| \Delta t$$

where: $|a_i|$ is the real time EMG value after amplification, band pass, and 60 Hz notch filter, digitalization and rectification, and $$\Delta t = t_{(i+1)} - t_i = 1/f$$

where f is the EMG Sampling Frequency, and

T=Δt N where N is the number of discrete points summed in the integration.

Let A*=the moving average process value, Then $$A^* = (1/M) \sum_{j=0}^{1-M} A_j$$

where M=the # of A values averaged. The filter averages the last M values of A.

If $T_{1/2}$=the shortest time in which A* can change by one half of its fulls scale amplitude, then $$T_{\frac{1}{2}} = M\left(\frac{T}{2}\right)$$

For example, if T=0.1 seconds and M=20, $T_{1/2}$ is (20× 0.1)/2 or 1 second. In some of our examples, T=3.2 ms and M=311, so $T_{1/2}$ is (311×0.0032)/2 or 0.5 seconds.

When using a integration time, e.g., 3.2 ms., that is short relative to the fastest muscular contractions, the first $a_i$ values grow gradually to the maximum value during the first 60 ms of the contraction. This initial slow rise in the integrated EMG signal limits the minimum response time of A*, but not significantly in our work.

The response of a single moving average process to large changes in input is linear. The time, $T_{1/2}$, it takes the control signal to change by half of its maximum value is approximated by the equation $T_{1/2} \approx (T)(M)(\frac{1}{2})$. In this equation, T equals the real time integration interval and M equals the number of points used by the moving average process.

The processed EMG signal output (NSUM) of the moving average process 17 is saved and used as input by an exponential average process 18. The new processed EMG signal output from the exponential average process, $A'_n$ (ANSUM) 18 is the sum of the current output of the moving average processor, $A^*_n$ (NSUM) 17 multiplied by a weighing factor, alpha, and of (1-alpha) times the previous ANSUM value.

$$A'_n = (\alpha)A^*_n + (1-\alpha)A'_{n-1}$$

The myo-control signal is generated by windowing processor 20 either NSUM or ANSUM. Sixteen windows, each corresponding to a myo-control signal level, are used. The windows are adjustable and set upper and lower limits for the processed EMG signal NSUM or ANSUM for each discrete control signal value. In order to minimize the impact of background EMG signal noise in the first level, 0 and to facilitate the return to the 0 control signal level, the first window width was set to approximately 140 points. The next three levels were set to slightly less than 100 points (80, 90, and 90, respectively). All other window widths were the same (i.e., each was 100 points for a total of 1600 points). Windowing 20 is a process by which fluctuating NSUM and ANSUM values are changed to a discrete control signal value over approximately 16 or 32 steps.

When NSUM is changing rapidly and NSUM and ANSUM values differ by at least one half of the width of the current window, then NSUM, the output of the moving average processor 17, determines the myo-control signal's magnitude, direction, and rate of change. The myo-control signal moves to the next level, up or down, when NSUM moves past the middle of the next window.

When NSUM and ANSUM are nearly equal (i.e., their difference is a value less than one half the width of the current window), then the more heavily damped output from the exponential process ANSUM 18 controls the myo-control signal level. In this case, the window in which ANSUM currently falls determines the myo-control output. When ANSUM moves to a new window, the my-control value changes.

Both auditory and visual feedback are provided to the operator. The visual feedback is a positional display on the computer monitor. This display has 16 windows or steps. There are 10 marked divisions within each window or step. This visual display shows the operator which window the EMG processed signal NSUM ($A^*_n$) is in and where, within that window, the signal value is located.

The auditory feedback is a tone whose pitch is determined by the discreet control signal output value (0–15). In addition to pitch, the processed EMG signal auditory feedback sound includes different tone quality color or timber. This characteristic of the auditory feedback sound is determined by the value or position of ANSUM with respect to the window currently determining the control signal value. There are three aural levels associated with each window.

Sample myo-control signals were generated from the right abductor pollices brevis, the tongue, the extensor carpi radialis, and the biceps brachii muscles of a single test subject. Active surface electrodes were placed over the motor endpoint of the muscle and a reference electrode was placed over a less electrically active area, e.g., for muscles of the right upper extremity the reference was the muscle tendon. In the case of the tongue, the active electrode was placed on the anterior aspect of the gum side of a mandibular splint. Amplifier gain settings were adjusted, for each muscle, to maximize the myo-control signal range.

FIGS. 10(A–D) depict the processing of the myo-control signal. FIG. 10(A) shows the amplified, band pass and 60 Hz notch filtered, real time EMG signal 22 recorded by the Nicolet Viking IV® EMG machine. Below the twenty second segment of real time EMG signal depicted at the top of FIGS. 10(B) and 10(C) show graphs of the control signals 24 and 26 after passing through the moving average processor (NSUM) or $A^*_n$ (FIG. 10(B) and then the exponential average process ANSUM $A'_n$ 18. FIG. 10(D) is a graph of the myo-control signal output, Win 20. The number of discrete output steps was limited to five in this depiction because of the relatively short recording time and the discrete gain setting of the Nicolet Viking IV machine.

Figure 11C:
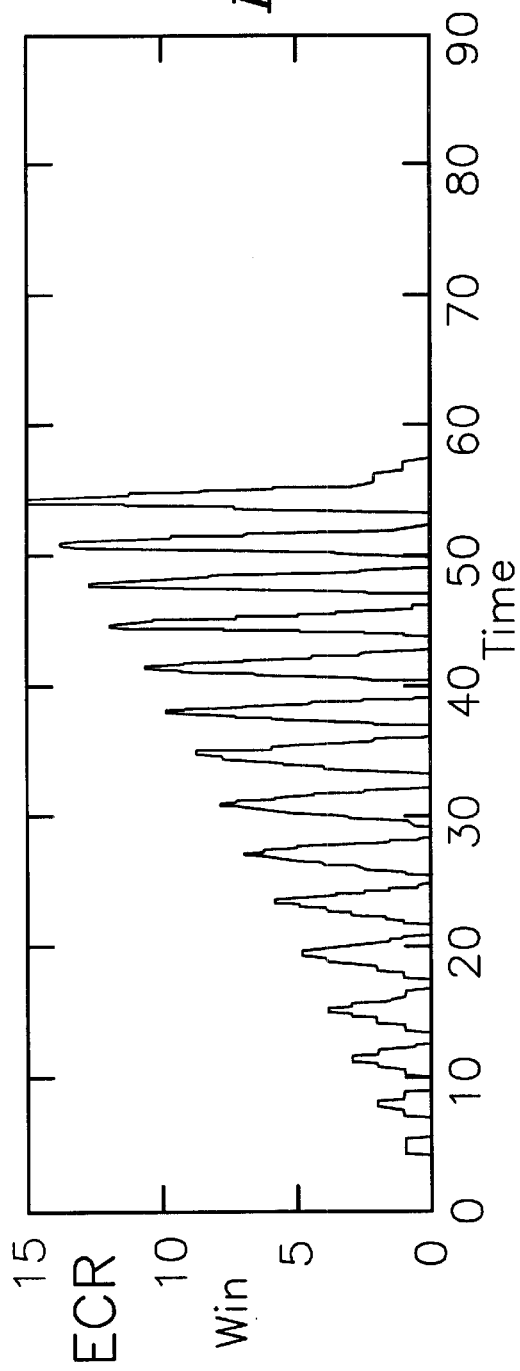
FIGS. 11(A–D) show four graphs from four different muscles illustrating brief on/off myo-control signals with increase in amplitudes.
Figure 11D:
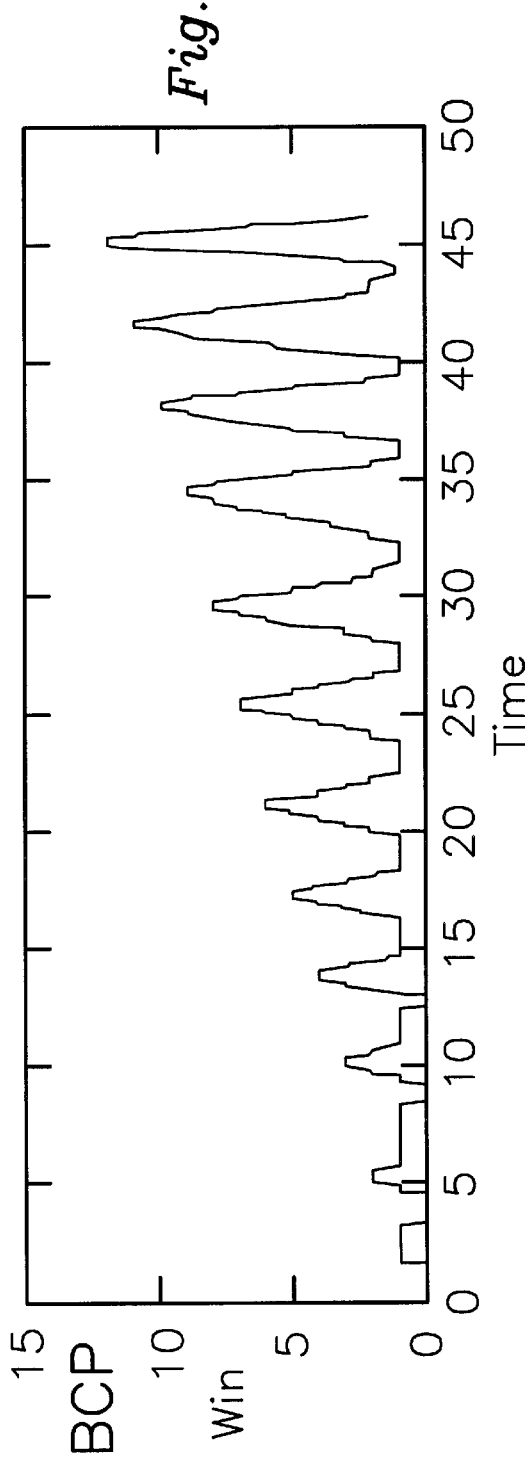
Figure 13A:
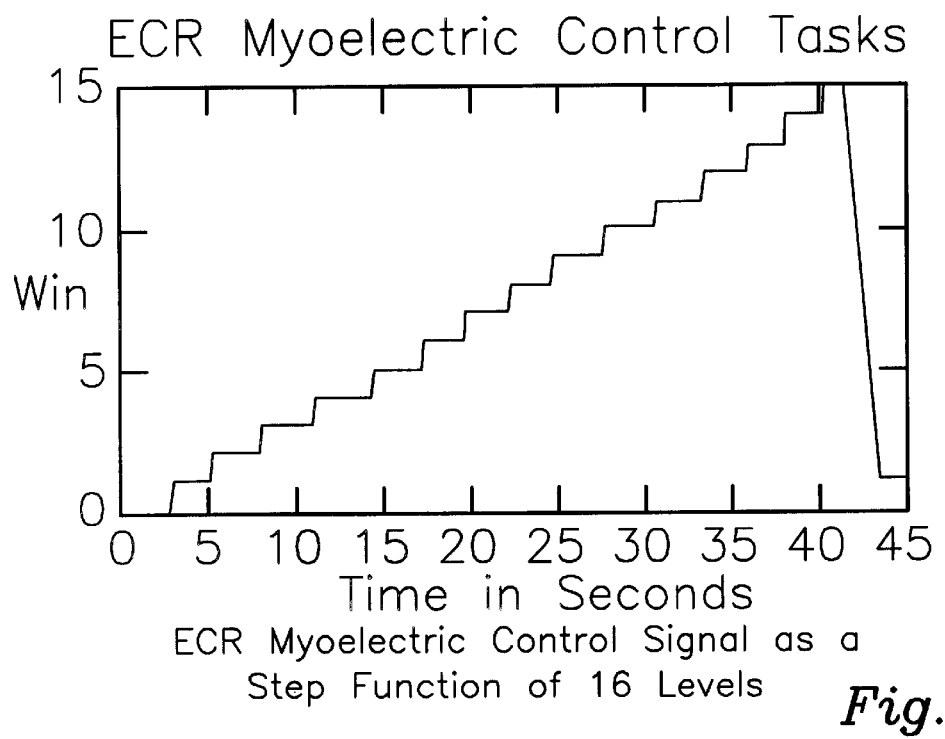
FIGS. 13(A–C) show three graphs which from top to bottom show ECR myoelectric control signals as a step function of 16 levels, ECR myoelectric control signals held at the 2, 6, 10 and 14 levels for about thirty seconds, and brief on/off ECR myoelectric control signals of increase in amplitude over 16 levels.
Figure 13B:
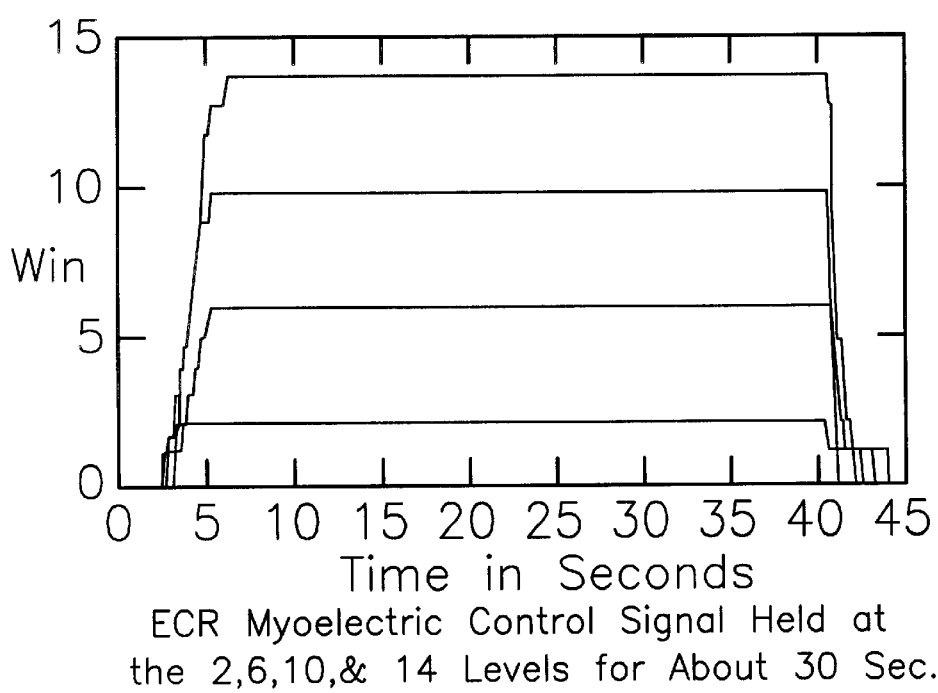
Figure 13C:
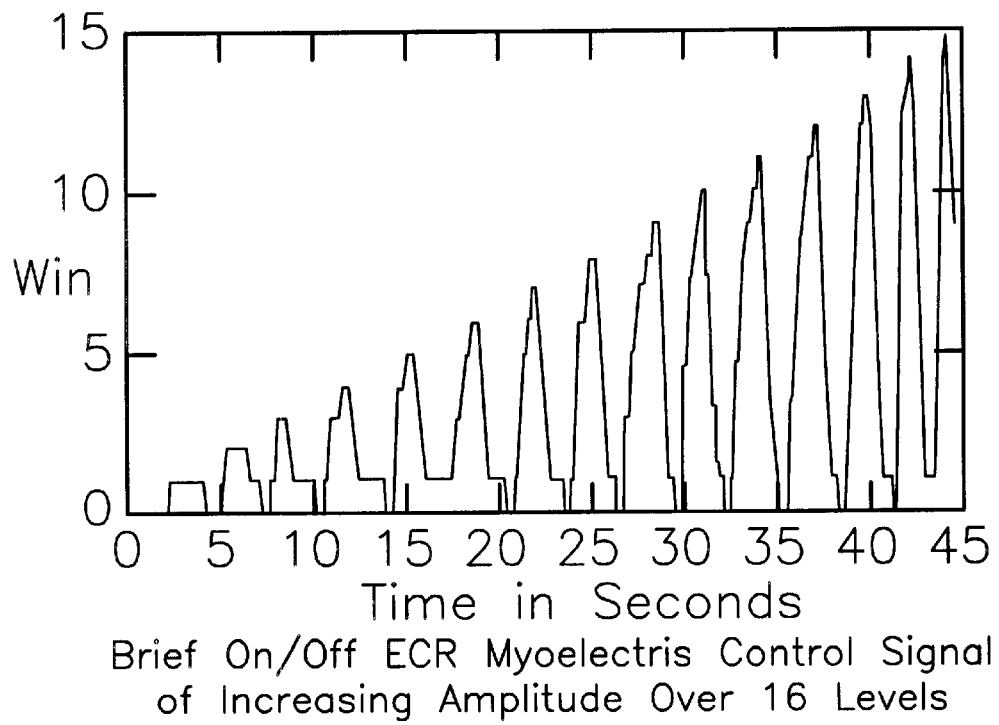
Figure 14A:
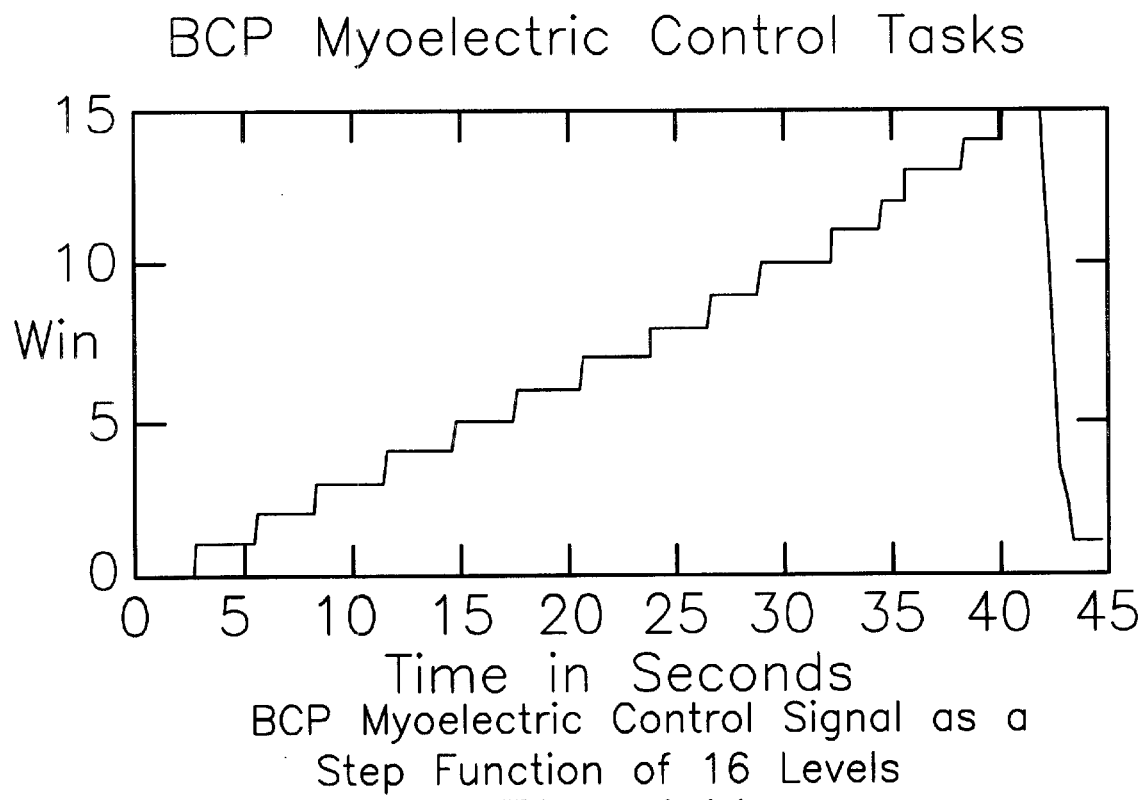
FIGS. 14(A–C) show three graphs which from top to bottom show BCP myoelectric control signals as a step function of 16 levels, BCP myoelectric control signals held at the 2, 6, 10 and 14 levels for about thirty seconds, and brief on/off BCP myoelectric control signals of increase in amplitude over 16 levels.
Figure 13D:
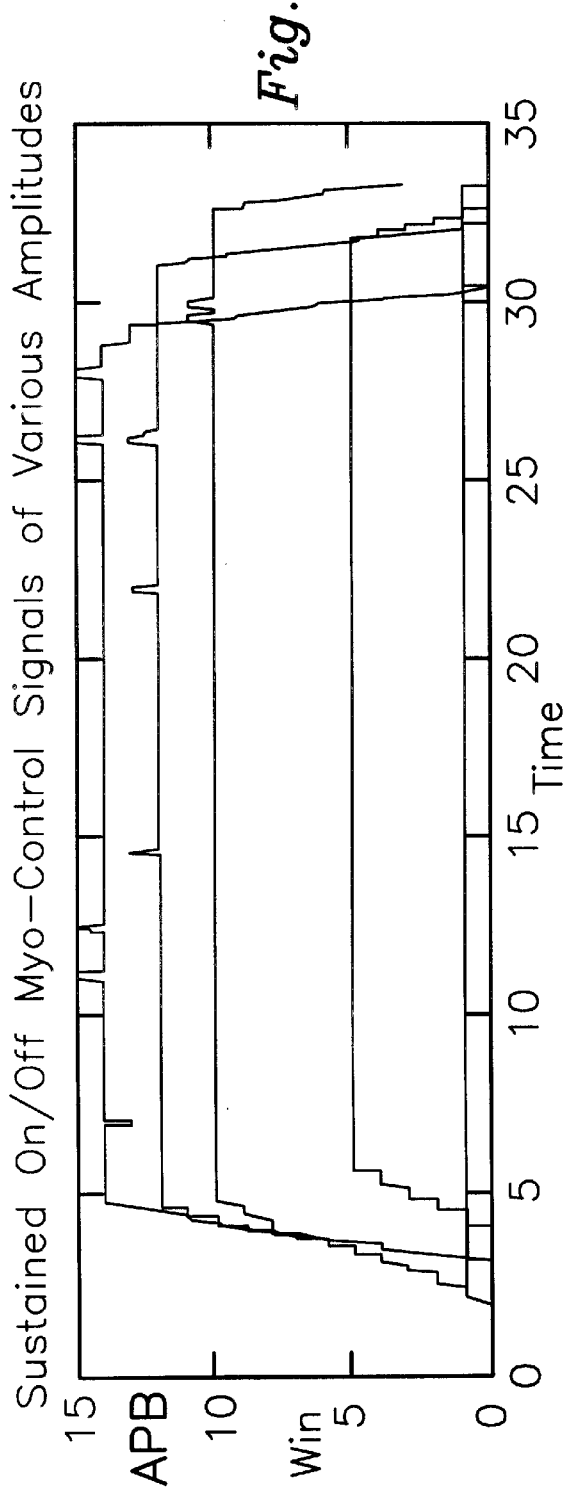
Figure 13E:
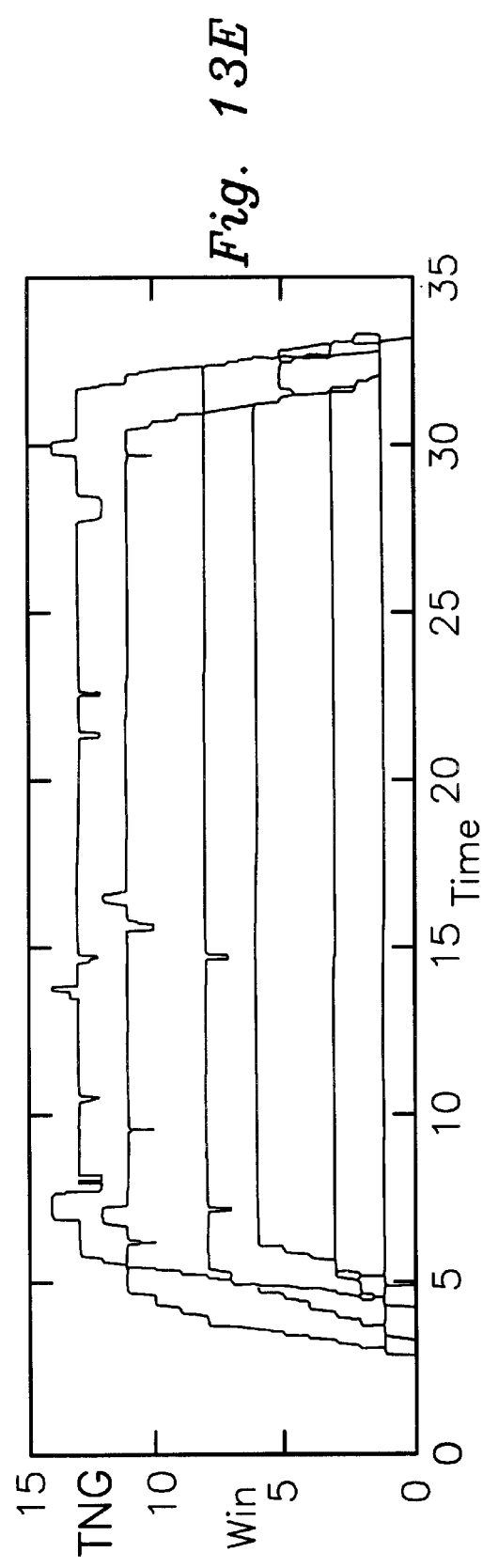
Figure 13F:
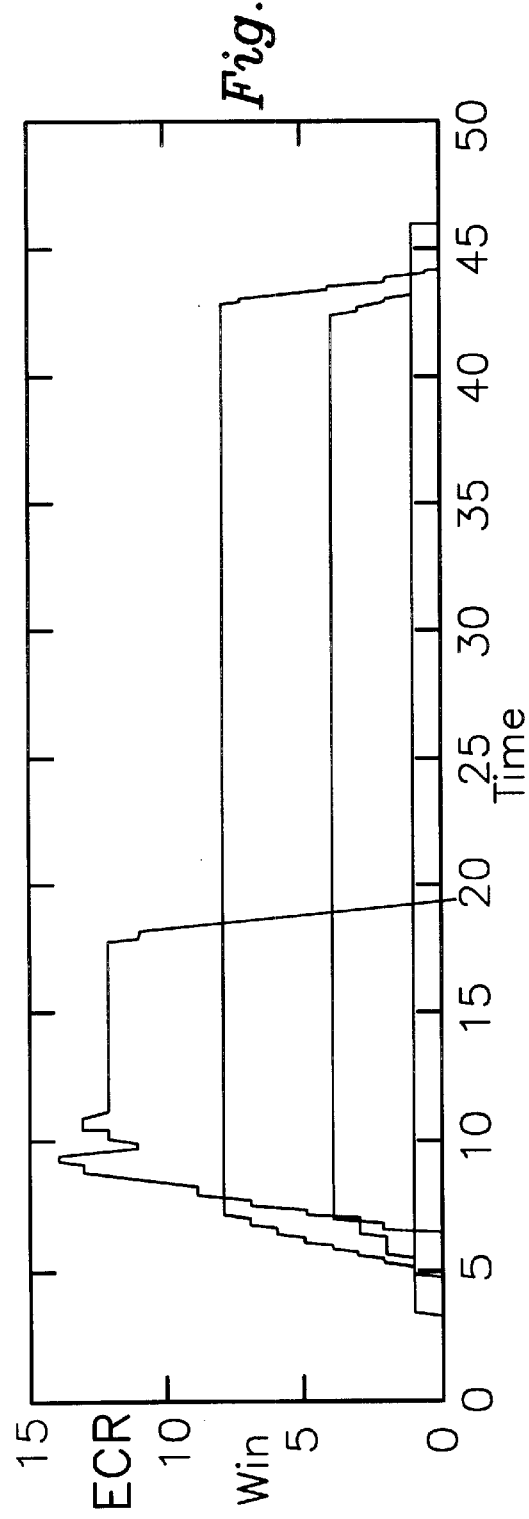
Figure 13G:
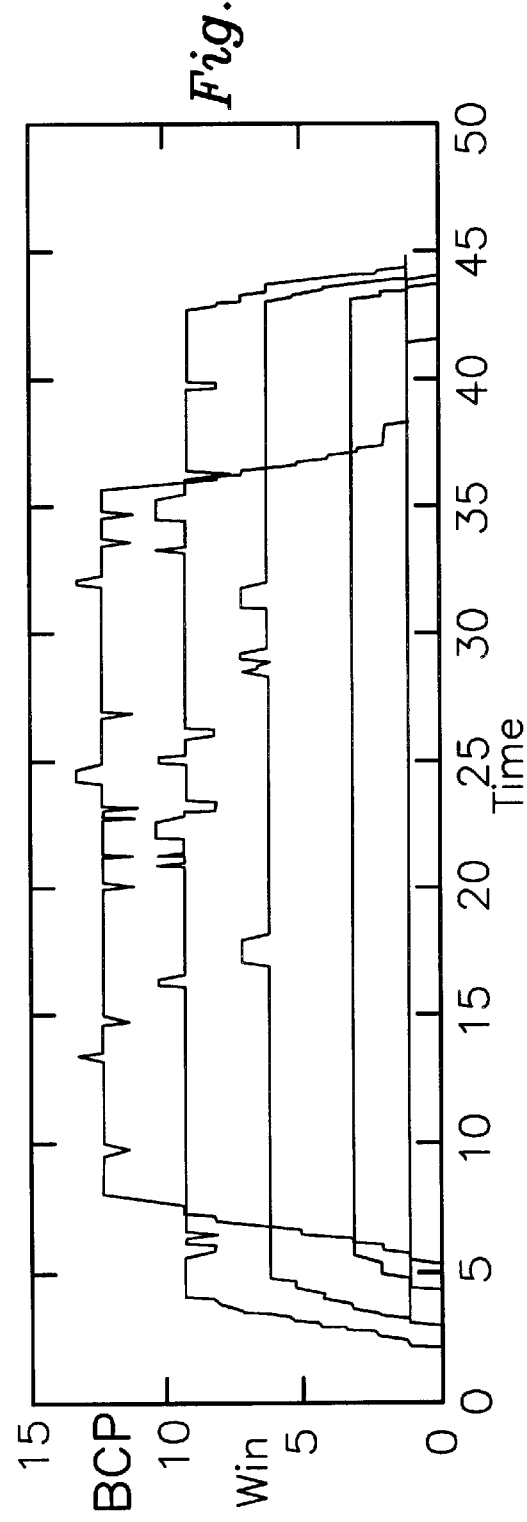
Figure 14B:
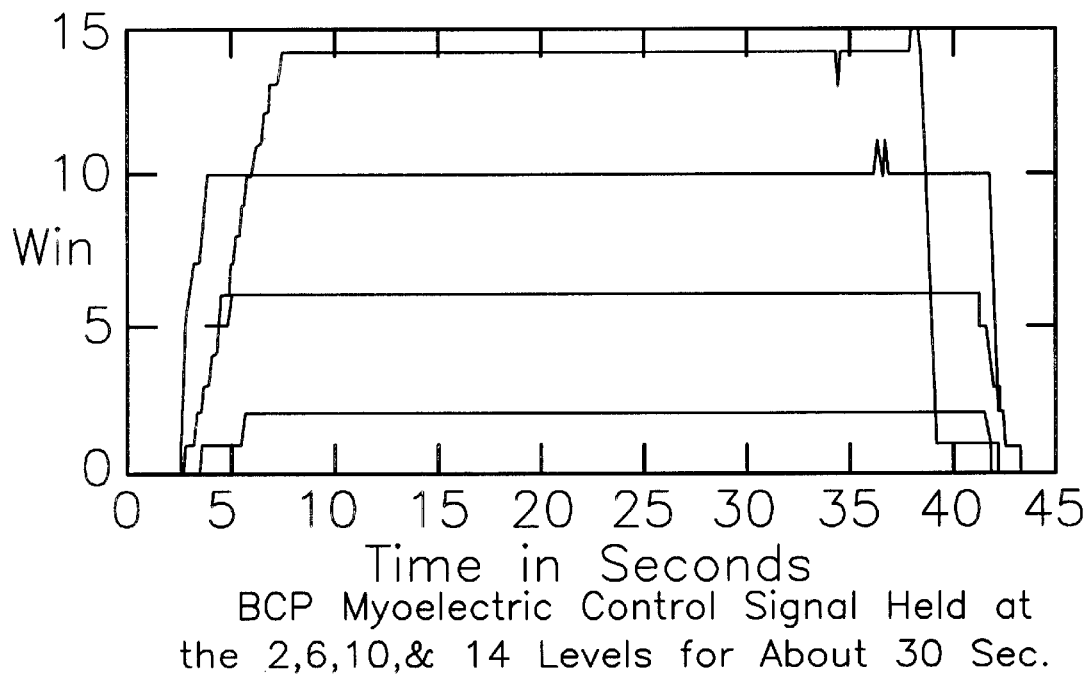
Figure 14C:
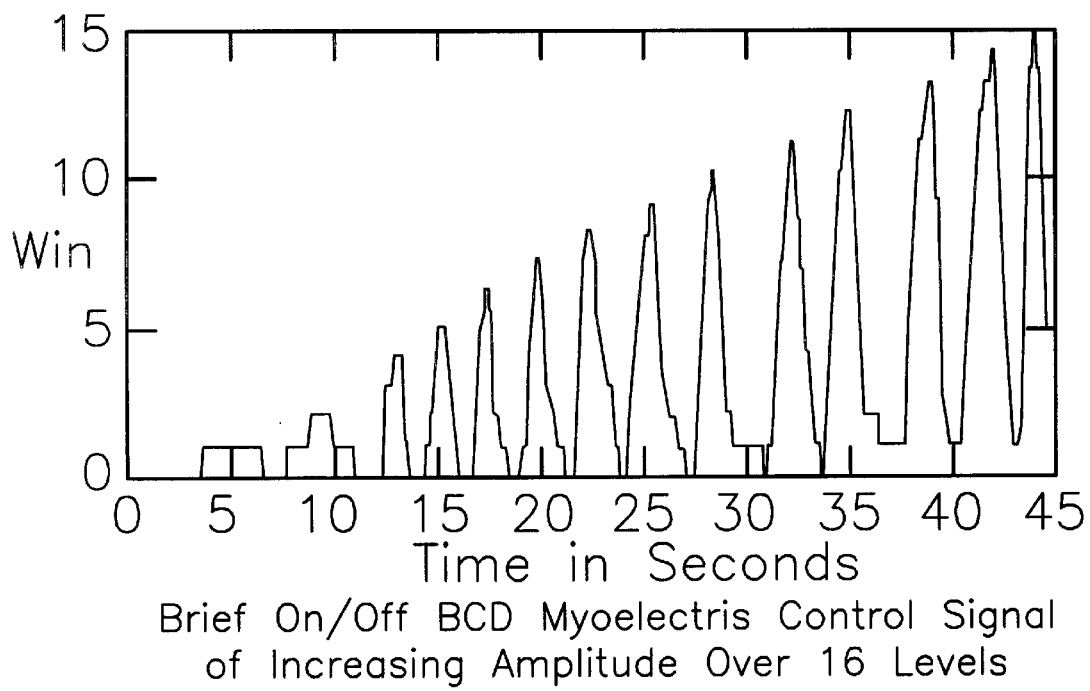
Figure 15A:
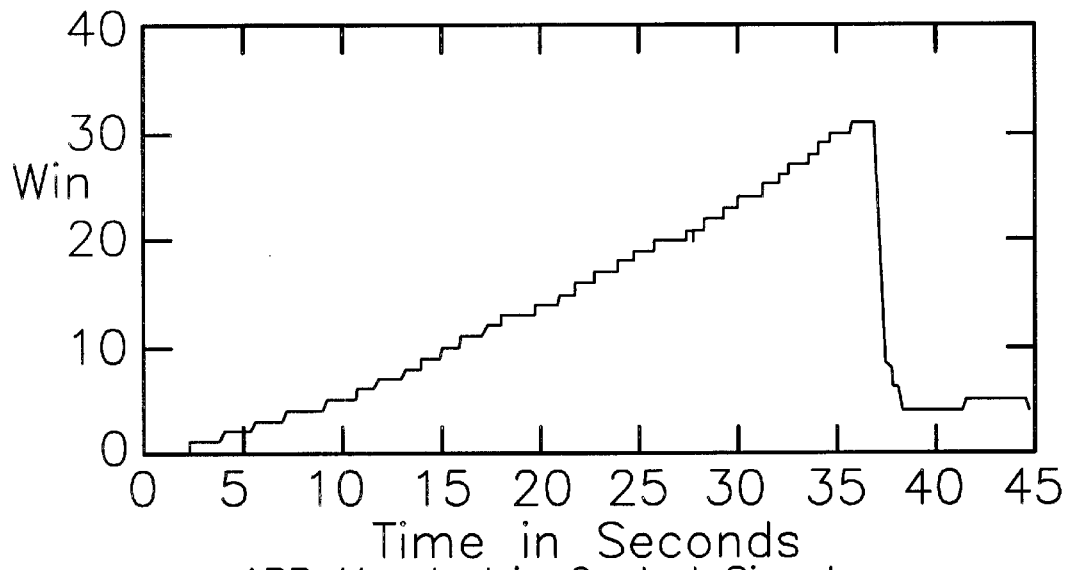
FIGS. 15(A–B) show two graphs which from top to bottom show APB myoelectric control signals as a step function of 32 levels, and BCP myoelectric control signals held at the 4, 12, 20 and 28 levels for about thirty seconds.
Figure 15B:
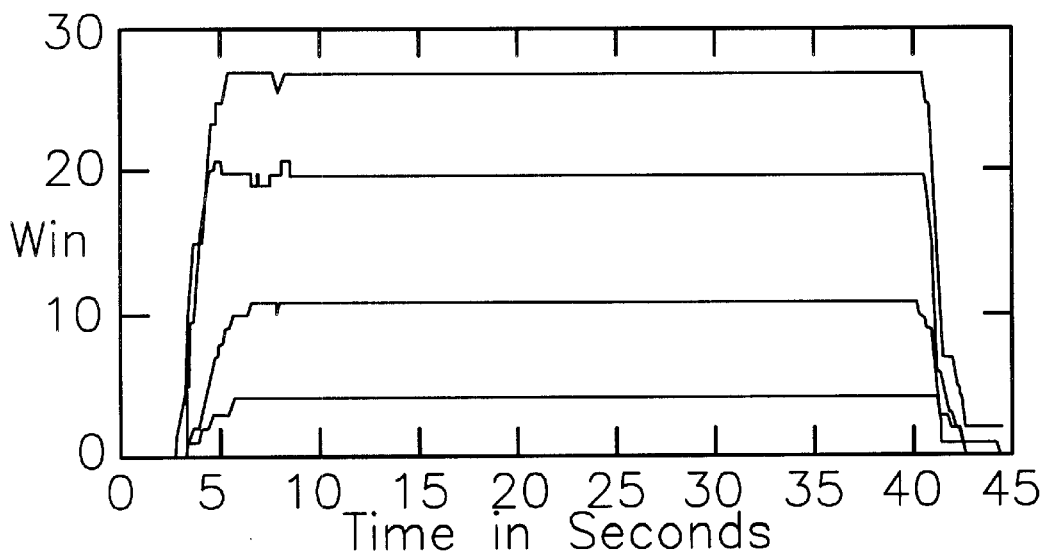

FIGS. 11(A–D) depict using a single moving average process of 311 points to generate a myo-control signal which increases rapidly to a target value and then returns rapidly to the baseline level. The target values increase sequentially from one to fifteen. The APB, TNG, and ECR myo-control signals spanned the range from zero to fifteen. There is more muscle EMG signal background present and this delayed the return to baseline. In the case of the biceps muscle, fewer discrete levels were obtainable (twelve) and electrical background noise was more of a problem.

FIGS. 12(A–D) depict using a single moving average process of 311 points for the task of myo-control signal steps of increasing amplitude. During this task each succeeding level is held approximately three to five seconds. APB, TNG, and BCP demonstrate fifteen myo-control signal levels. With each of these muscles, slight instability occurred for higher level control signals. During the ECR muscle tests, stable sustained steps above twelve could not be obtained using a single moving average process of 311 points.

FIG. 13 depicts the task of generating myo-control signals which increase rapidly to a target value and then hold that value for a prolonged period of time. The APB and TNG graphs demonstrate good control stability though most of the control range with signal instability increasing as maximum voluntary muscle contract is approached. The ECR graph shows excellent stability at lower levels, but significant instability at the, maximum achievable, myo-control level of twelve. This level was not sustainable for more than ten seconds. The BCP graphs shows an earliest onset of instability than the other graphs.

It has been found that one may dynamically vary the number of moving average process points as a function of the rate of change of the integrated EMG signal to improve myo-control signal stability and increase the number of discrete levels of control by using the adaptive moving average process illustrated in FIGS. 1(A–B) and 2.

An adaptive process changes its behavior to adapt to changing input. The Adaptive Moving Average Process (AMAPr) 28 changes the number of points it averages in response to the nature of its input 30. The nature of the input is determined by the rate at which the output of a simple moving average process of moderate length changes. If that rate is low, than the AMAPr 28 will attempt to use more points to increase the smoothing of its output. If that rate is high, the process will attempt to use fewer points to improve responsiveness. Parallel processes 32, 34, 36, 38, and 40, each averaging a different number of points, are used. Process 32 samples the most points and processor 40 samples the fewest points. Since the process cannot see future points, it must look farther into the past to increase the number of points. Since recent data motivated the change, less recent data may reverse the change and this can lead to unstable behavior. The AMAPr uses discrete size steps as it changes size and, when it becomes longer, time delays are used to ensure that the process output remains stable.

The AMAPr performs multiple moving average processes using a single input buffer. This buffer is used to store the input values over a time interval determined by the product of the sampling rate and the number of points in the buffer. This buffer is circular so that the time interval represented by the samples in the buffer remains constant. The buffer holds points reaching back in time at least as far as the largest moving average process to be performed. This circular buffer is constructed by using pointers representing the most recent and least recent samples in the buffer. These pointers move through the buffer, so that, once the buffer is filled, each new sample replaces the oldest sample in the buffer.

Each moving average process 32–40 covers a different time interval, which overlap, and each process uses the most recent sample, pointed to by the head pointer, as the front end of its time interval. Each process has its own tail pointer which moves through the buffer in step with the head pointer, so that each process looks at samples from a fixed period of time. The processes whose tail pointers stay farther behind the head pointer look at more samples, including samples from farther back in time. As a result, these longer interval processes provide more smoothing but are less responsive than the shorter interval processes.

The AMAPr adapts its behavior to the behavior of the input signal 30. When the input signal is changing rapidly, the overall process output should follow that rapid change as closely as possible. This requires that averages over a shorter interval of time be used to generate the output. When the input signal is changing slowly, a longer interval of time should be used in the moving average process to increase stability.

The output from one of the middle length processes, such as processor 38, is differentiated by differentiator 42 in order to produce a binary control signal which is used to modify the behavior of the overall process in response to changes in the input signal. When the input signal is changing rapidly, the differentiated signal becomes larger than a preset threshold. This indicates that the overall process output 44 should be taken from successively shorter moving average processes. When the differentiated signal goes below that same threshold, the overall output is taken from successively longer moving average processes. These adaptations continue until the longest or shortest process is selected or the nature of the input signal changes.

The rate at which the successively shorter processes are selected is rapid in order to help the overall output follow sudden changes in input. The rate at which successively longer processes are selected is slower in order not to introduce instability caused by incorporating information from times prior to the period of less change. The parameters for the threshold, the delay before switching to a shorter process, and the delay before switching to a longer process are all adjusted to optimize overall process characteristics.

Figure 2:
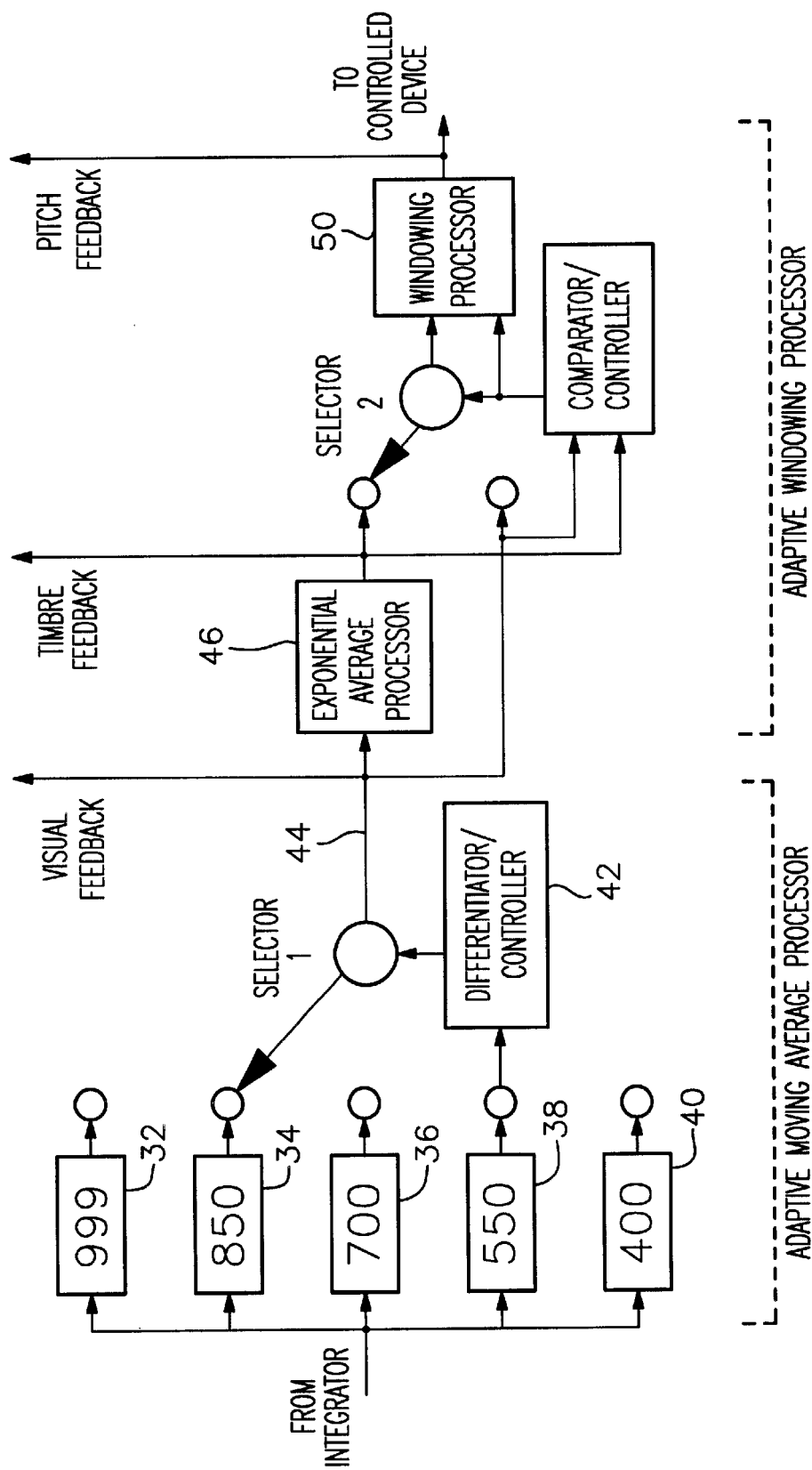
FIG. 2 is a schematic diagram of a portion of the diagram of FIGS. 1(A–B)
Figure 21C:
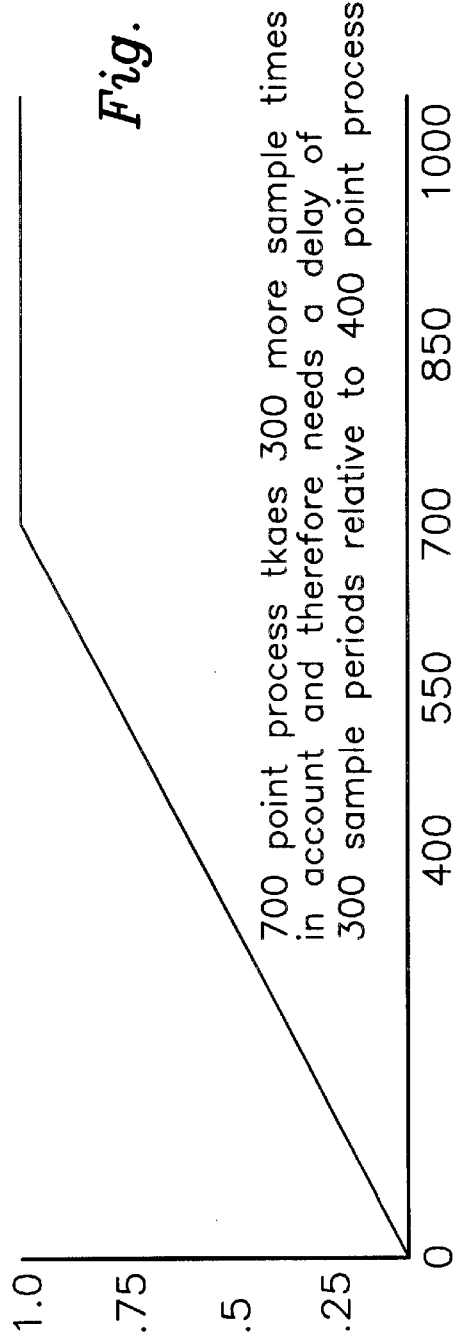
FIGS. 21(A–D) show four graphs illustrating the switching delays when switching between parallel processors shown in FIGS. 1A–B and 2.
Figure 21D:
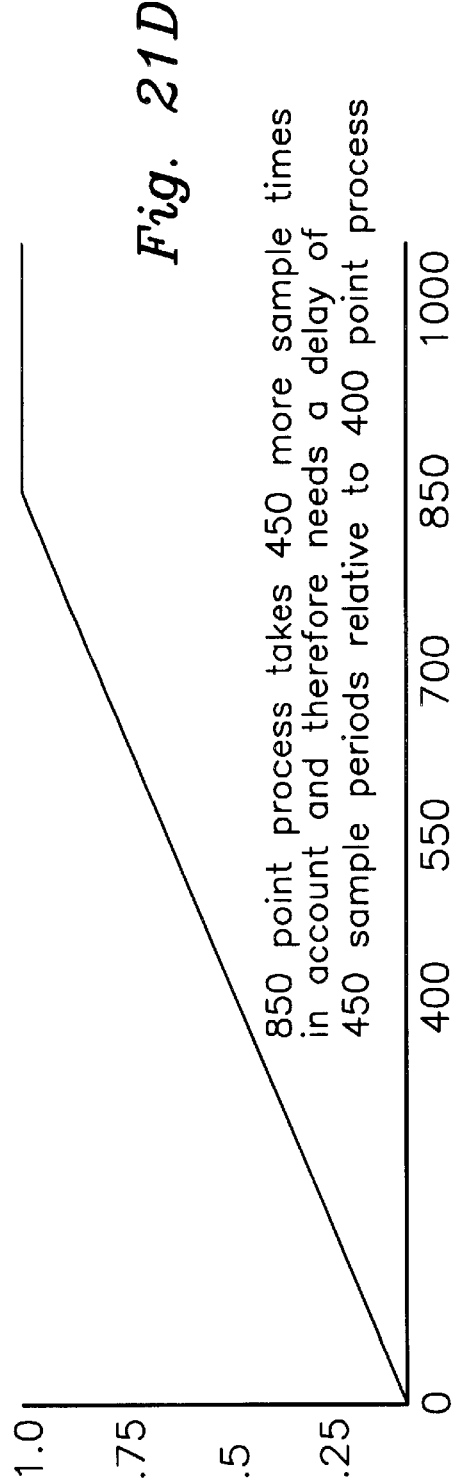

The minimum switching delay between the parallel processes, shown in FIG. 2, is 150 sampling times. The 400 point process 40 takes 400 sample times to respond to step input. The 550 point process 38 takes 150 more sample times into account and therefore needs a delay of 150 sample periods relative to the 400 point process. The 700 point process 36 takes 300 more sample times into account and therefore needs a delay of 300 sample periods relative to the 400 point process. The 850 point process 34 takes 450 more sample times into account and therefore needs a delay of 450 sample periods relative to the 400 point process. These various delays are illustrated by the graphs shown in FIGS. 21(A–D).

As previously indicated, smoothing of the integrated stored signals 30 is accomplished by the first component of an adaptive moving process 28 including a set of parallel moving average processes 32–40, as shown in FIGS. 1(A–B) and 2.) The number of moving average process points that can be used for a given signal integration time interval is limited by the desired responsiveness of the processed myoelectric control signal.

The response of a single moving average process to changes in input signal amplitude is linear. The time, $T_{1/2}$, it takes the control signal to change by half of its maximum value is approximated by the equation $T_{1/2} \approx (T)(M)(\frac{1}{2})$. In this equation, T equals the real time integration interval (0.8–3.2 msec., usually, in our system) and M equals the number of points used by an individual moving average process. For small integration time intervals (T=0.8 msec.), dynamically varying the moving average process used by the overall adaptive processor permits response times of less than 400 msec. full scale (i.e., 15–32 levels per 400 or so msec.) for large, rapid signal changes and good stability for small, slower changes.

In order to improve control signal stability and at the same time retain the responsiveness of the myoelectric control signal system, the band passed and notch filtered, rectified and integrated EMG signals are passed through five moving average processes 32–40 simultaneously. Each process has a different number of moving average process points, 400, 550, 700, 850 and 999. Each process generates an NSUM value, one of which is chosen to be the output of this adaptive process 28. The processed myoelectric signal NSUM has the unit of Volt-seconds (actually microvolt-seconds) because the EMG signals are integrated with respect to time before signal processing by the moving average processor. Most myoelectric control signals used previously with prostheses, however, have had the units of Volts.

The adaptive moving processor closes down (i.e., changes to a moving average process with a fewer number of points) during periods of rapid change of the rectified and integrated surface EMG signal amplitude (up or down). Conversely, the adaptive moving average processor opens up (i.e., changes to a moving average process using a greater number of points) more slowly during periods of slow or no change of the integrated surface EMG signal amplitude. When the program starts, the NSUM value used as the output of the adaptive moving average processor comes from the 999 point process 32.

A rate of change for NSUM is computed using the 550 point moving average process 38. An NSUM value from the 550 point moving average process is sampled every 100 msec. and the changes are compared to an adjustable threshold value (in our system, set at 33 points per 100 msec.). When the absolute value of the difference between two NSUM values separated by 100 msec. exceeds this threshold, the adaptive moving process starts closing down toward 400 points. When the threshold is not reached, the adaptive moving average processor starts opening up toward 999 points. The chosen threshold value is equal to approximately 20 percent (i.e., 330/1600 of the maximum rate of change of NSUM). The threshold value is determined empirically for our system by a trial and error method. After a preset delay, this process is repeated.

As previously indicated, time delays are used to control the rate of opening and closing of the adaptive processor. The delays for opening and closing are set independently and are different. The delay used for opening of the adaptive process (i.e., increasing the number of process points) is roughly five times longer than the delay for closing of the adaptive process (i.e., decreasing the number of process points). The switching time between processes for opening is on the order of tenths of seconds and for closing is on the order of hundredths of seconds.

As moving average processes with fewer numbers of points are chosen, the system responds faster. This process continues until the 550 point process 38 is in use, or until the rate drops back below the threshold. When the rate of change goes back below the preset threshold, the switching process is reversed. The system then switches (with a longer delay) through successively larger moving average processes, and the system response slows down. The delays which determine how rapidly the system switches between moving average processes of different length and the rate of change threshold which controls the direction of this switching are adjusted to optimize the system's behavior. This computer controlled switching of moving average processes gives the user of the myoelectric control system better control and stability for small changes in control signal amplitude, which are typically made slowly, while retaining a faster response for larger changes in myoelectric control signal amplitude. The use of two or more parallel moving average processes in this way is referred to as an adaptive moving average process (AMAPr).

The processed EMG signal output (NSUM or A*) 44 of the selected moving average process is saved and used as the input by an exponential average process (ANSUM or A') 46. A mathematical description of the exponential average process (ANSUM or A') is set forth below.

Let A'=the output of an Exponential Average Process whose input is A*
Then $$A'_n = (\alpha)A^* + (1-\alpha)A'_{n-1}$$

where $\alpha$=weighing constant for Exponential Average Process, $A'_n$ is the current value of A', and $A'_{n-1}$ is the previous value of A'. This process' response is easy to adjust by varying $\alpha$. One can use an $\alpha$ of 0.00313, which gives a time constant of roughly 320 T or about 1 second for the current system where T=3.2 msec. This process is used after the moving average process, and its output signal amplitude changes more slower than the moving average processes signal amplitude output to changes in the EMG signal.

The new processed EMG signal output 48 from the exponential average process (ANSUM or A') is the sum of the current output of the adaptive process (NSUM or A*) multiplied by a weighting factor, alpha, and (1-alpha) times the previous ANSUM value.

When NSUM is changing rapidly and, as a result, NSUM and ANSUM values differ by at least one half of the width of the current window, then NSUM, the output 44 of a adaptive moving average process, determines the myoelectric control signal's amplitude, direction, and rate of change. The myoelectric control signal moves to the next level, up or down, when NSUM moves past the middle of the next window.

When NSUM and ANSUM are nearly equal (i.e., their difference is a value less than one half the width of the current window), then the more heavily damped output 48 from the exponential filter process 46, ANSUM or A', controls the myoelectric control signal level. In this case, the window in which ANSUM currently falls determines the myoelectric control signal output. When ANSUM moves to a new window, the myoelectric control signal value changes.

The myoelectric control signal is generated by windowing 50 either NSUM or ANSUM. Windowing 50 is a process by which fluctuating NSUM and ANSUM values are changed to discrete myoelectric control signal values. Currently, either 16 or 32 windows, each corresponding to a myoelectric control signal value, are used. The windows are adjustable and set upper and lower limits for the processed EMG signal NSUM or ANSUM for each discrete myoelectric control signal value. In order to minimize the impact of background EMG signal noise in the first level, 0, and to facilitate the return to the 0 control signal level, the first window width was set to approximately 140 points. The next three levels were set to slightly less than 100 points (80, 90, and 90 points, respectively). All other window widths were the same (i.e., each was 100 points for a total of 1600 points) over the 16 levels. For the 32 level windowing processor, each window has a width which is one half that of the 16 level windowing processor. The last process of the myoelectric control signal system is referred to as an adaptive windowing process (AWPr).

The output 44 of the Adaptive Moving Average Process (AMAPr) 28 is one of two possible inputs to the Adaptive Windowing Process (AWPr). The AWPr produces a stabilized output (window value) with a fixed number of possible values. This process, like the AMAPr process, adapts itself to the behavior of the incoming data in such a way as to increase stability when that data is changing slowly and to allow less stability when the data is changing rapidly.

In the AWPr, an exponential average process is used to produce a more heavily damped myoelectric control signal output from the AWPr processor. The output of the adaptive moving average processor, AMAPr 44, is labeled NSUM in the algorithm. The exponential average process output 48 is labeled ANSUM. NSUM, ANSUM, and the previous window value are used by the AWPr to determine the new window output value.

A new value of ANSUM, the output of the exponential average process, is calculated from the previous value and the current value of NSUM using a weighing factor alpha:

$$ANSUM = (1-\alpha)^* ANSUM + \alpha^* NSUM$$

In the AWPr, the window value from the previous period is saved in lwin. then NSUM, is used to find a tentative new window value, win. Below is a section of the code:

```
// start of code segment
// save the old value lwin=win;
// find a tentative a new value
win=0;
for(j=15;j>0;j--)
if(NSUM>w[j])
{
win=j;
break;
}
// end of code segment
```

The output changes to the tentative window value determined by NSUM when that NSUM value is beyond the center of one of the windows adjacent to the previous window. This allows rapid motion through many windows but prevents jumping back and forth between adjacent windows when the control value is jittering near the edge.

```
// start of code segment
if (win>lwin && NSUM<c[lwin+1]) wind=lwin;
else if (win<lwin && NSUM>c[lwin-1]) win=lwin;
// end of code segment
```

The previous code segment handles the case where NSUM is changing rapidly. When NSUM is not changing rapidly, AWPr's output should change to the new window only when the, heavily damped, ANSUM has moved out of the previous window. This allows slow motion between windows when NSUM moves into and stays in a new window for about 1/(alpha) sample times. W is an adjustable parameter used to define the threshold for rapid change in NSUM. Since ANSUM is much more heavily damped than NSUM, rapid change can be defined as the situation when the absolute value of their difference exceeds a threshold. Below is another section of the code.

```
// start of code segment
if (abs(ANSUM-NSUM)<W && !((ANSUM>w[win+
   1]) && (w[win+1]>\ NSUM) || (NSUM>w[win]) &&
   (w[win]>ANSUM)))
{
if win<15 && ANSUM>w[win+1]) win=win+1;
else if (win>0 && ANSUM<w[win]) win=win -1;
}
// end of code segment
```

Both auditory and visual feedback are provided to the user 51. The visual feedback is a positional display on the computer monitor. This display has either 16 or 32 windows or levels. There are ten marked divisions within each window or step. Visual display shows the operator which window the EMG processed signal NSUM is in and where, within that window, the signal value is located.

For the myoelectric control signal data, the 16 step Win process was expanded to 32 steps. The actual control windows are half as large (50 points vs 100 points) as in the 16 step program. The display was expanded to four rows and wrapped around on the screen and the visual feedback still has ten divisions marked within each step.

The auditory feedback is a tone whose pitch is determined by the myoelectric control signal output value, Win, (0–15 or 0–31). In addition to pitch, the processed EMG signal auditory feedback sound includes different tone qualities or timbres. This characteristic of the auditory feedback sound is determined by the value or position of ANSUM with respect to the window currently determining the control signal value. There are three aural timbres associated with each window, one for the bottom third and below, another for the middle third, and the last for the upper third of the window and above.

EXAMPLE

A technique used in clinical medicine for positioning surface EMG electrode pairs was used in order to maximize the differential EMG signal input to the high impedance amplifier. The active electrode input to the differential amplifier is recorded from over the motor end plate of the muscle and the reference electrode input is recorded from over a neutral location (i.e., either over a tendon or tendon insertion to a bone). The distance between the electrodes varies depending on the anatomy of the individual being tested.

Sample myoelectric control signals were generated from the right abductor pollices brevis (APB), the extensor carpi radialis (ECR), and the biceps (BCP) muscles of a normal male test subject, age 49. Active surface electrodes were placed over a less electrically active area (for the abductor pollices brevis muscle, the reference electrode was placed over the proximal phalangeal metacarpal joint; for the extensor carpi radialis muscle, the reference electrode was placed over the lateral epicondyle; and, for the biceps muscle, the reference electrode was placed over the distal biceps tendon at the elbow). Amplifier gain settings were adjusted for each muscle to maximize the myoelectric control signal range. Myoelectric control signals were recorded from three muscles in one test subject in order to demonstrate the same recording and signal processing techniques for three muscles of different size and location on the body and with different ratios of nerve fibers to muscle fibers. Myoelectric control signals were recorded from the right abductor pollices brevis muscle of three additional normal test subjects, two males, ages 52 and 10, and one female, age 17.

FIGS. 10(A–D) depict the processing of the myoelectric control signal beginning with the amplified, band pass and 60 Hz notch filtered, EMG signal recorded by the Nicolet Viking IV P® EMG machine. The moving average process control signal, NSUM, is depicted below the 20 sec. segment of real time EMG signal. The middle graph is the control signal after passing through the exponential average process, ANSUM. The bottom graph of FIGS. 10 (A–D) of the myoelectric control signal output, Win. The number of discrete output steps was limited to five because of the relatively short recording time and the available gain settings of the Nicolet Viking IV machine. During this recording, the M (moving average process points) used to generate NSUM was fixed at M=311.

Figure 10A:
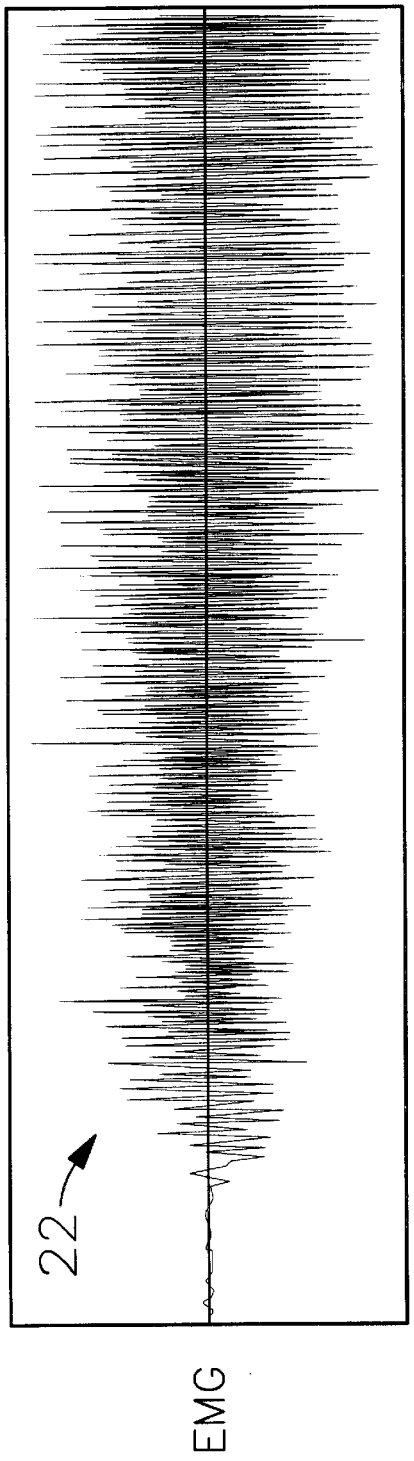
FIGS. 10(A–D) show are graphs illustrating the processing of EMG signals in accordance with this invention.
Figure 10B:
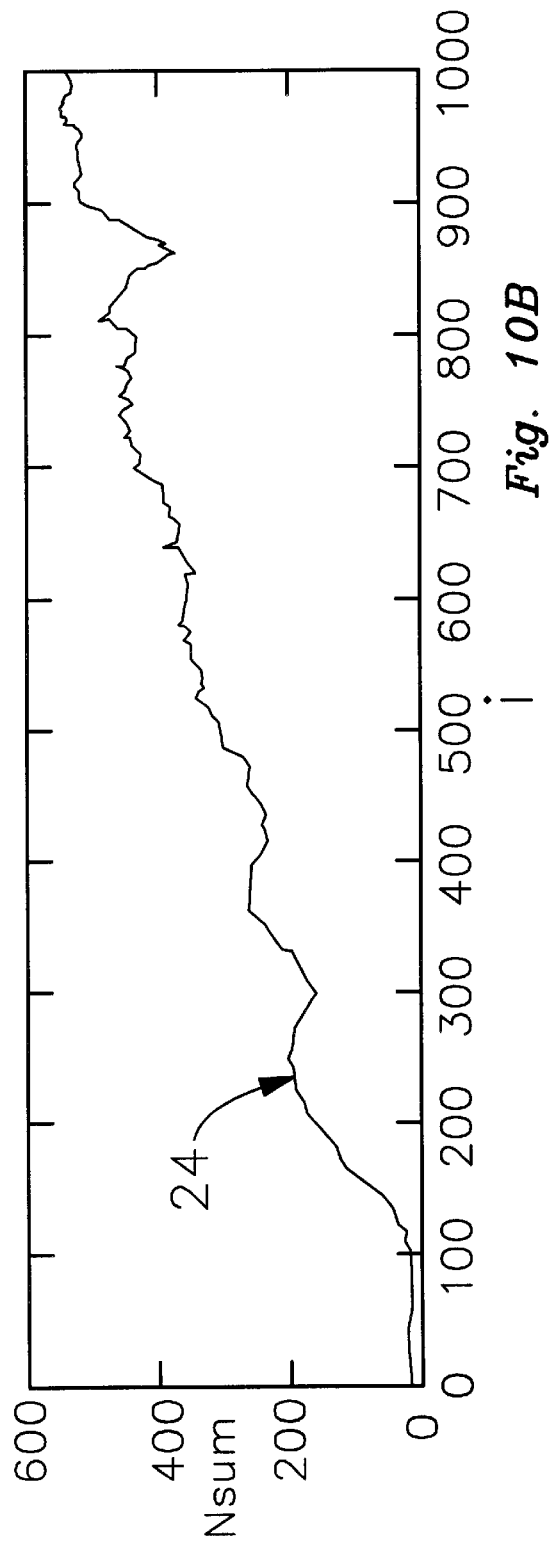
Figure 10C:
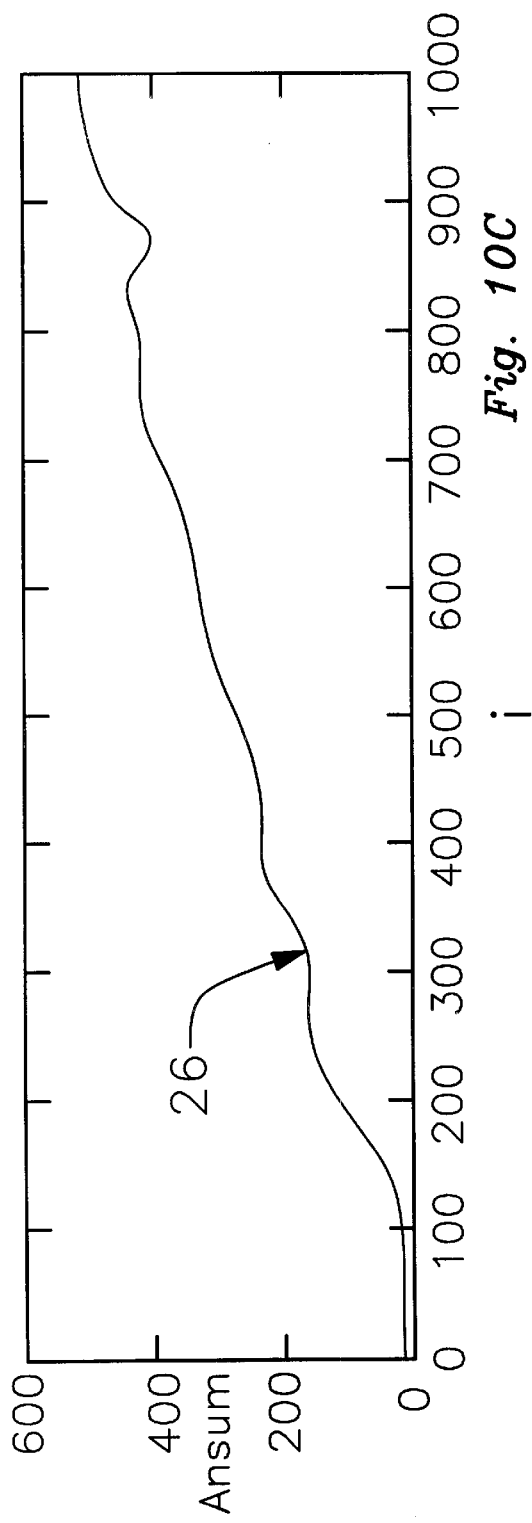
Figure 10D:
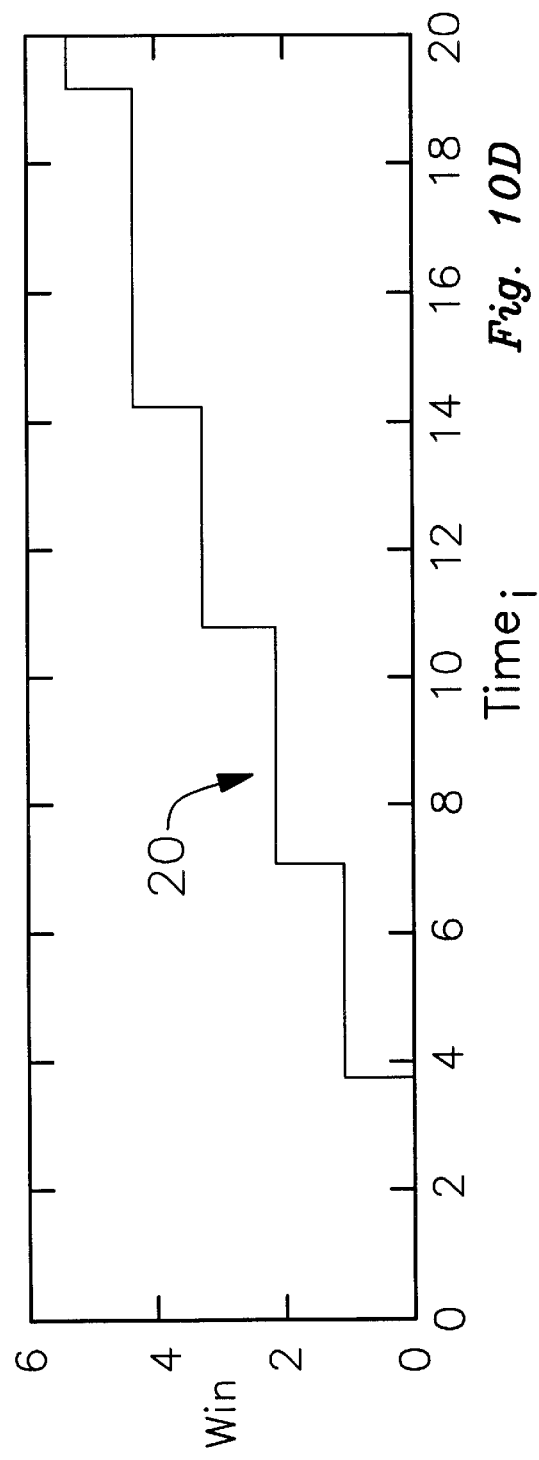

The mild clipping at the end of the EMG graph of FIG. 10(A) is an artifact of the Viking IV display process. The clipping was not present in the signal going from the Viking IV EMG machine to our A/D conversion board. The output of the portable grass preamplifier was also kept below the maximum input values of the A/D board to prevent clipping.

FIGS. 13(A–C), 14(A–C) and 15 depict two or three myoelectric control tasks performed by three muscles (abductor pollices brevis, APB, extensor carpi radialis, ECR, and biceps, BCP) in one test subject. The first task requires the generation of a 16 or 32 level myoelectric control step function, the second task demonstrates holding a myoelectric control signal at discrete levels for at least 35 sec., and the third task demonstrates brief sequential on/off myoelectric control signals of increasing amplitude over 16 levels. During the third task, relaxing the muscle quickly to the 0 level is sometimes difficult.

The 0 state contains background electrical noise, as well as background EMG signal noise. It takes almost complete relaxation of the muscle to enter the 0 level and this is more difficult during a rapid time test (i.e., the subject must perform and track a precise contraction 16 times in 45 sec.).

Figure 16A:
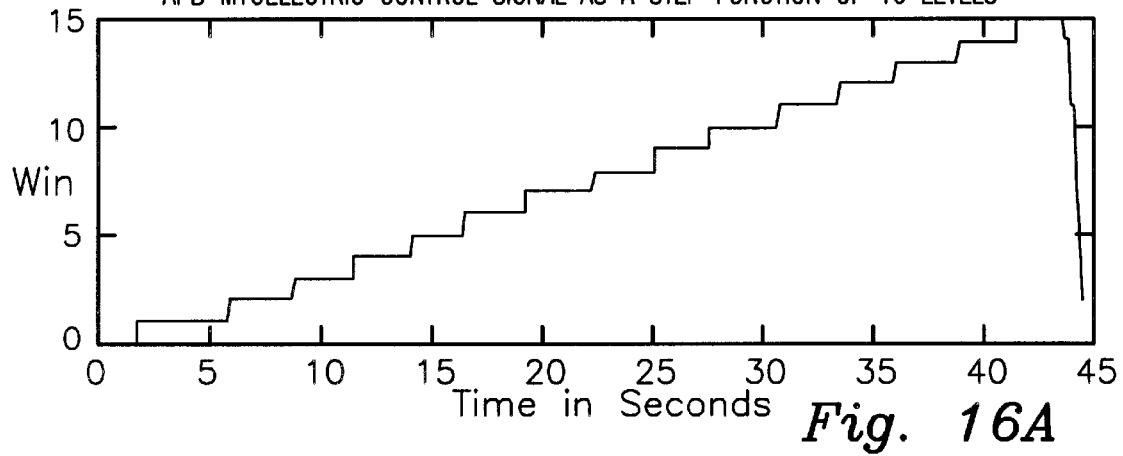
FIGS. 16(A–C) show three graphs which from top to bottom show APB myoelectric control signals as a step function of 16 levels, brief on/off APB myoelectric control signals of increasing amplitude over 16 levels, and APB myoelectric control signals held at the 2, 6, 10 and 14 levels for about thirty seconds.
Figure 16B:
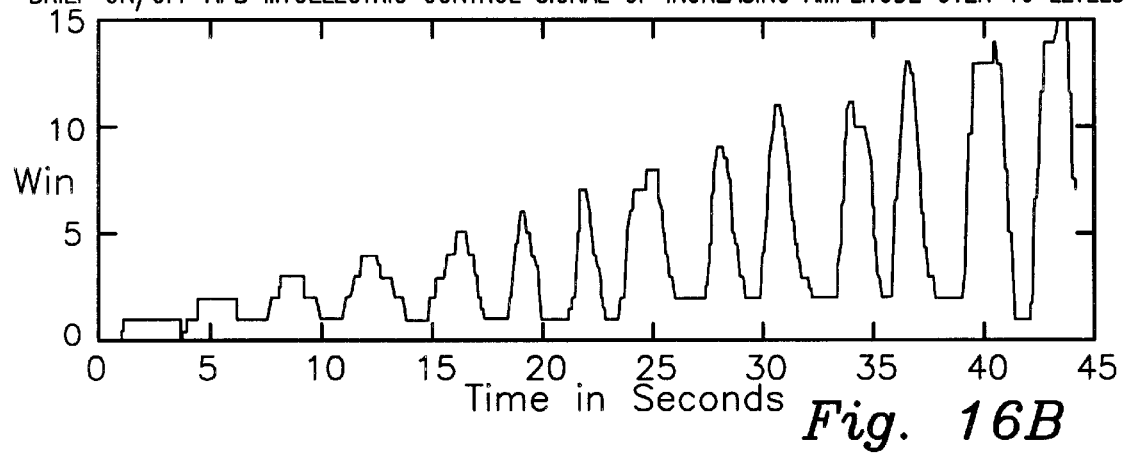
Figure 16C:
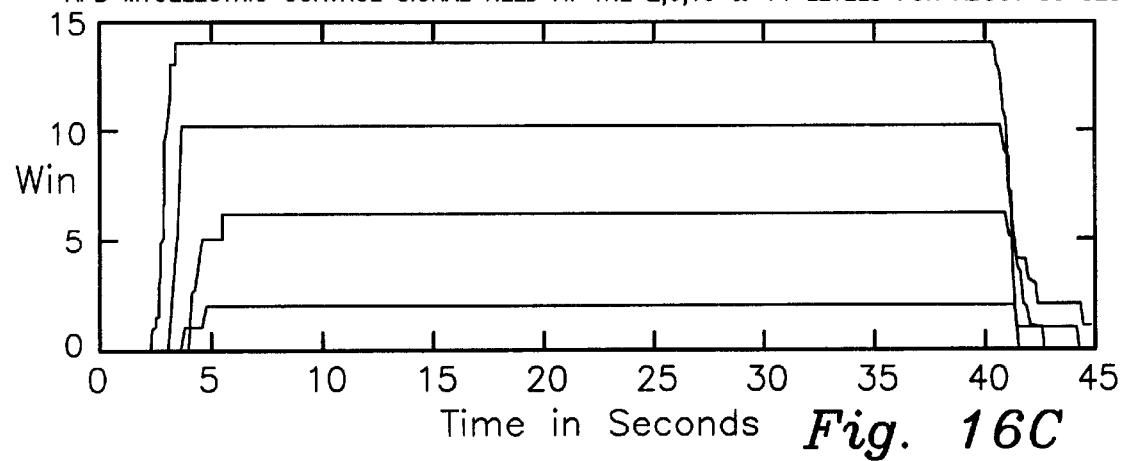
Figure 17A:
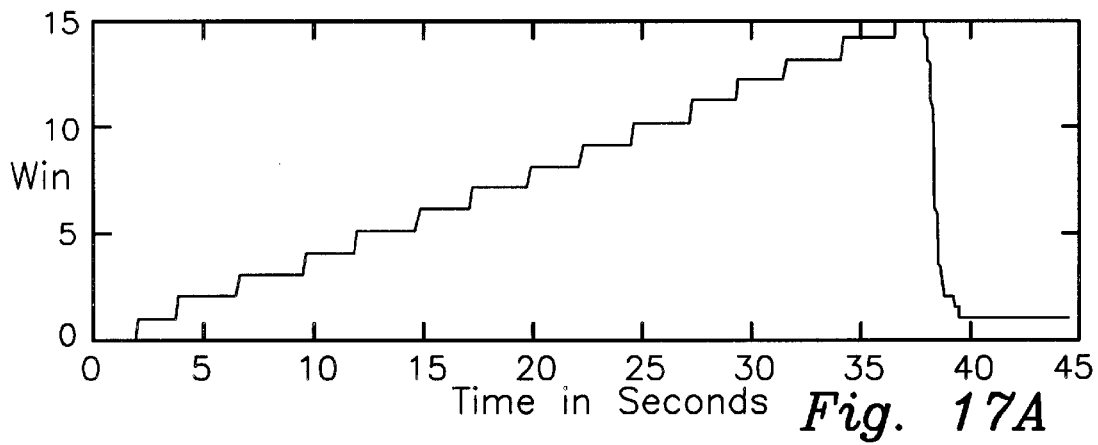
FIGS. 17(A–C) show three graphs which from top to bottom show APB myoelectric control signals as a step function of 16 levels, brief on/off APB myoelectric control signals of increasing amplitude over 16 levels, and APB myoelectric control signals held at the 2, 6, 10 and 14 levels for about thirty seconds.
Figure 17B:
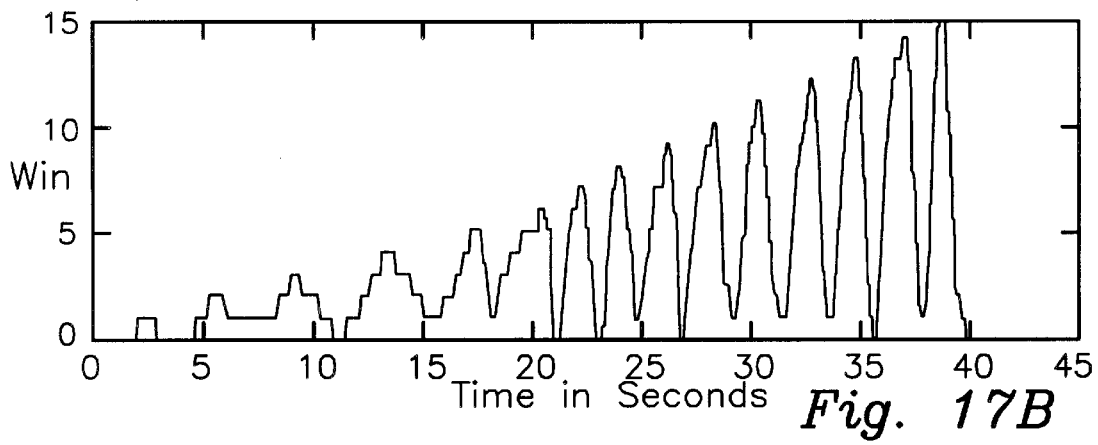
Figure 17C:
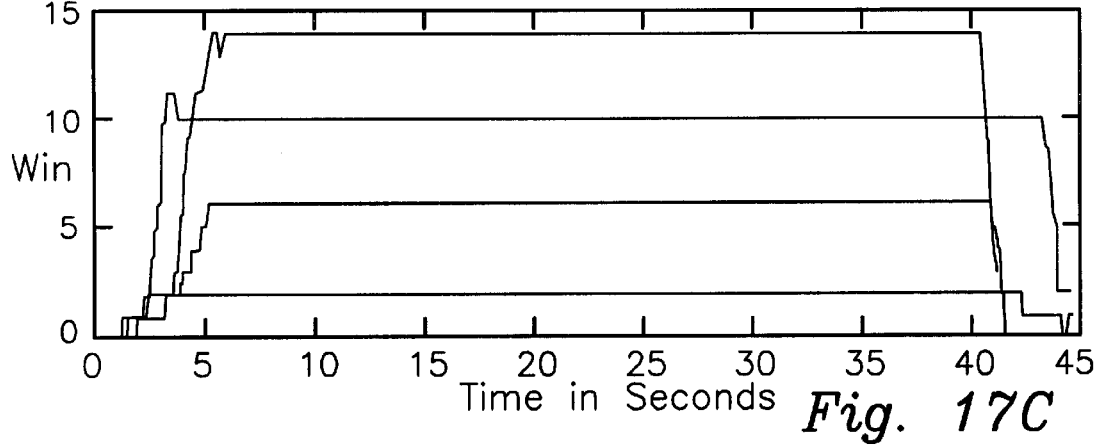
Figure 18A:
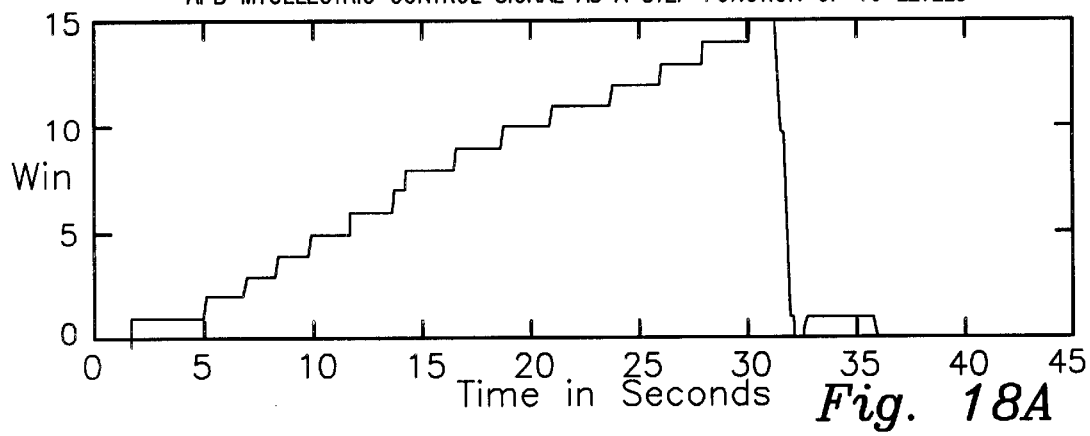
FIGS. 18(A–C) show three graphs which from top to bottom show APB myoelectric control signals as a step function of 16 levels, brief on/off APB myoelectric control signals of increasing amplitude over 16 levels, and APB myoelectric control signals held at the 2, 6, 10 and 14 levels for about thirty seconds.
Figure 18B:
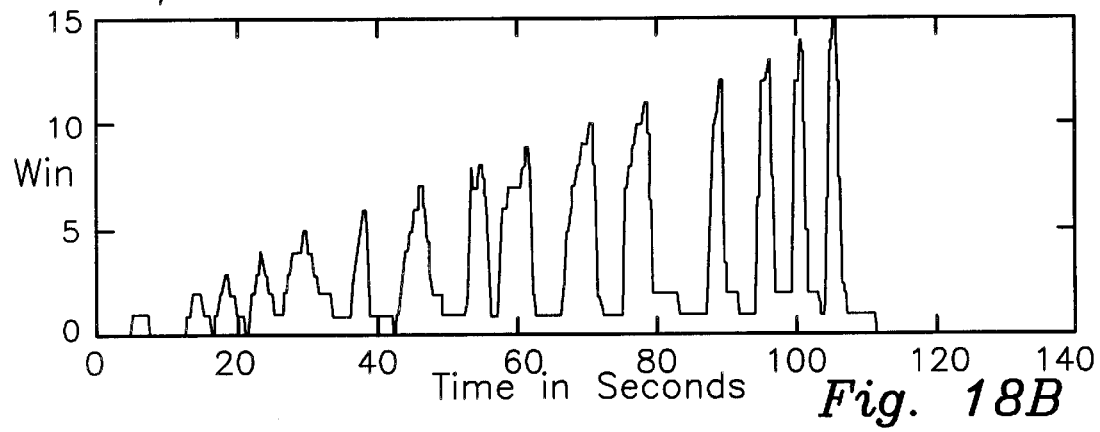
Figure 18C:
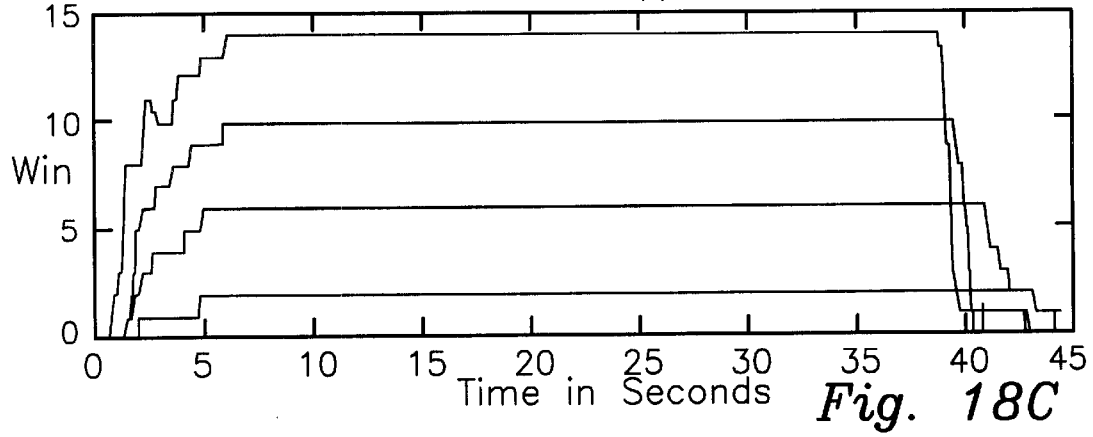

FIGS. 16(A–C), 17(A–C) and 18(A–C) demonstrate the results from three additional normal test subjects: a male, age 52; a female, age 17; and a male, age 10. The first test subject (male, age 52) required a total of 1.5–2.0 hours divided into two sessions to learn how to perform the three tasks. The second subject (female, age 17) required 1.5 hours in one session, and the third subject (male, age 10) required 2.5–3.0 hours divided into three sessions to perform the three tasks. All four test subjects could achieve 16 levels of control and hold that control for 30–35 sec. The 10 year old test subject required a significantly longer period of time (about 106 sec. rather than 45 sec.) to demonstrate a brief sequential on/off myoelectric control signals of increasing amplitude. The 52 year old male test subject had the most difficult time completely relaxing during the generation of the brief sequential on/off myoelectric control signals of increasing amplitude.

One system limiting factor is the time it takes the computer to perform its tasks in real time. The computer must do all of its activities, including signal processing and providing visual and auditory feedback, during a very small time interval (0.8–3.2 msec.) in order to remain in real time. This time restraint becomes even more of a consideration when simultaneously processing multiple channels. Integrating the filtered, digitalized and rectified EMG signal prior to processing of the signal by the moving average process provides additional smoothing of the signal with very little additional computer processing time. The faster computers that are now available will allow the testing of even smaller integration intervals and greater numbers of moving average process points with the same or improved responsiveness. Either the use of smaller integration intervals or the use of non-integrated signal samples is possible, but such use may introduce greater signal variability.

The use of an exponential average processor 46 further stabilizes the myoelectric control signal when NSUM and ANSUM are close in value. Varying the exponential process constant, alpha, as a function of the rate of EMG signal change, was not done in this system, but may also be used to advantage in increasing myoelectric control signal stability and the number of discrete myoelectric control levels.

The use of a series of adjustable windows allows the conversion of the processed EMG signals into discrete values. Although all the windows are adjustable in the 16 or 32 step process, only the first four windows in the 16 step filter process (140 points, 80 points, 90 points, and 90 points) were set differently to compensate for EMG signal background noise. The remaining 12 windows were set at 100 points each. Because of the nonlinear nature of motor unit recruitment (surface EMG signal production) and the change in surface EMG signal power spectrum with muscle fatigue, the use of variable window widths throughout the range of 16 or 32 steps should theoretically improve myoelectric control signal stability. Except at the very low end of the amplitude range, preliminary testing of variable window widths did not consistently improve myoelectric control signal stability.

The overall responsiveness of the myoelectric controller system, when going from 0 signal to the maximum signal (step 15 or 31), with this system is approximately 320 msec. for T=0.8 msec. and 1280 msec. for T=3.2 msec. ($T_{1/2}$=160 to 640 msec.). When the type of sensory biofeedback (visual, auditory, or somatosensory) and human cortical processing time are taken into consideration, the maximum rate of change in level over the range of the controller may be more important than the absolute time it takes to go from the resting, or 0, state to the maximum amplitude level. For a myoelectric controller with three levels and a full scale responsiveness of 400 msec., it would take approximately 200 msec. to go from level 0 to 1 and 200 msec. to go from level 1 to level 2. This might be perceived as slow control. Even in a five level controller, the time required to go from level 0 to level 1, 1 to 2, 2 to 3, or 3 to 4 would be 80 msec. which may also be perceived as too long a time.

In a myoelectric controller with 16 levels and a full scale responsiveness of 400 msec., the operator or user would perceive the velocity or rate of change between individual levels as considerably faster (i.e., 15 levels per 400 msec., or about 27 msec. to move between levels). When 32 levels of control are used, the operator or user perceives very rapid change (31 levels per 400 msec., or about 13 msec. to move between levels). Regardless of the form of feedback used, a human cannot process information and make decisions at these fast rates. Instead, the operator or user must anticipate the control level desired and slow down considerably before arriving at that level. The current speed of the controller, in terms of the rate of change of control levels, should be adequate for many limb movements, as well as for the performance of many activities of daily living. To generate very fast prosthetic movements, such as those which occur in limbs during innate or conditioned reflexes, preprogrammed movements with very fast response times may be necessary.

For the myoelectric controller techniques presented herein, an attempt has been made to provide precise visual and auditory feedback in order to discover the number of stable myoelectric control signal levels that can be realized. Only after the application of these techniques to specific control tasks using appropriate feedback for the task will the value of the techniques be know.

Sixteen stable myoelectric control signal levels are easily achieved using the system digital process described herein. Thirty-two myoelectric control signal levels can be resolved, although not yet with adequate stability and control, particularly when the EMG signal is changing rapidly during an up/down task and when an M of less than 400 points is used by the adaptive moving average process producing NSUM. The use of smaller integration intervals and the use of four 100 point moving average processes in series in place of the 400 moving average process and the use of larger maximum moving average processes (1100 to 1500 or so) may further improve myoelectric control signal responsiveness and stability, and increase the number of stable myoelectric control signal levels to more than 32. It has been estimated that up to 45 command levels is desired for dexterous hand grasp in a neural prosthesis.

The use of the new, more sophisticated adaptive EMG signal processing technique describer herein provides 16–32 discrete myoelectric control signal levels which can be held stable for 30 sec. or longer. The adaptive moving average and windowing processes used in this system also adjust myoelectric control system responsiveness and stability based on system conditions in order to maximize system performance. Initial integration of the filtered, rectified, and digitalized EMG signals provides additional smoothing without loss of responsiveness when computer cycle time (i.e., time required for data processing and providing feedback to the operator) approximates the integration interval or data sampling interval.

Figure 4:
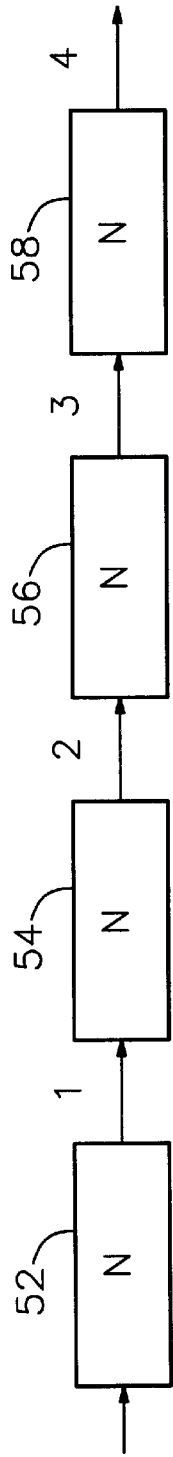
FIG. 4 is a schematic diagram of an alternative embodiment of the parallel moving average processor shown in FIG. 2.
Figure 5:
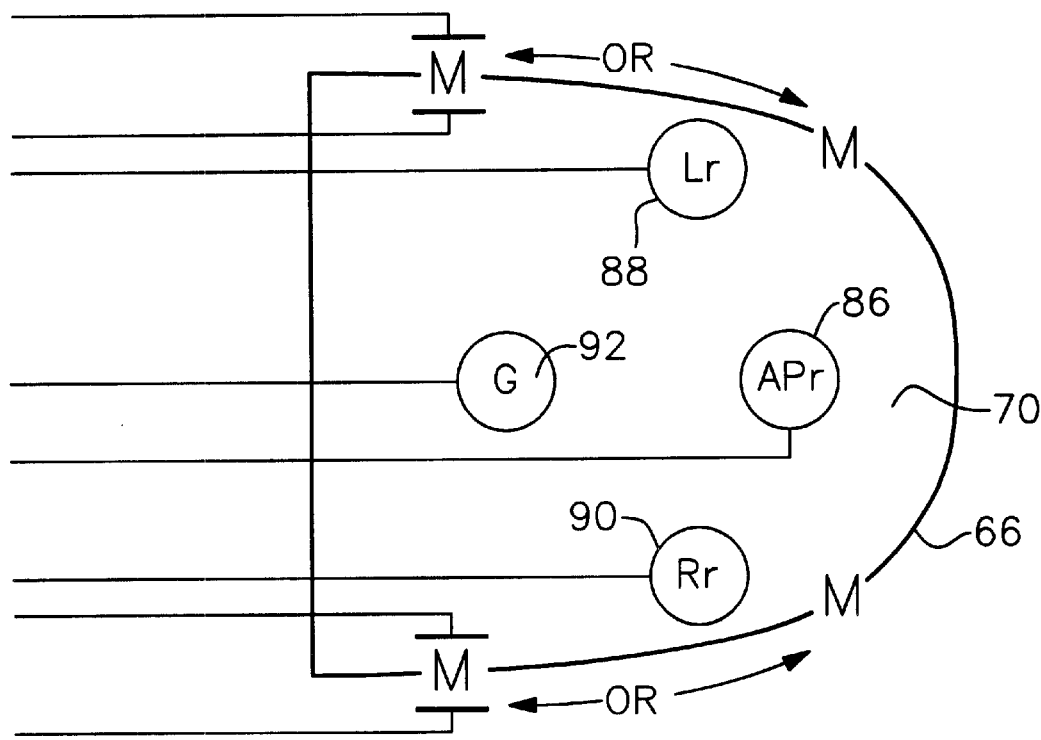
FIG. 5 is a top plan view of the maxillary splint portion of the intraoral device of this invention showing the palate side of the splint.
Figure 6:
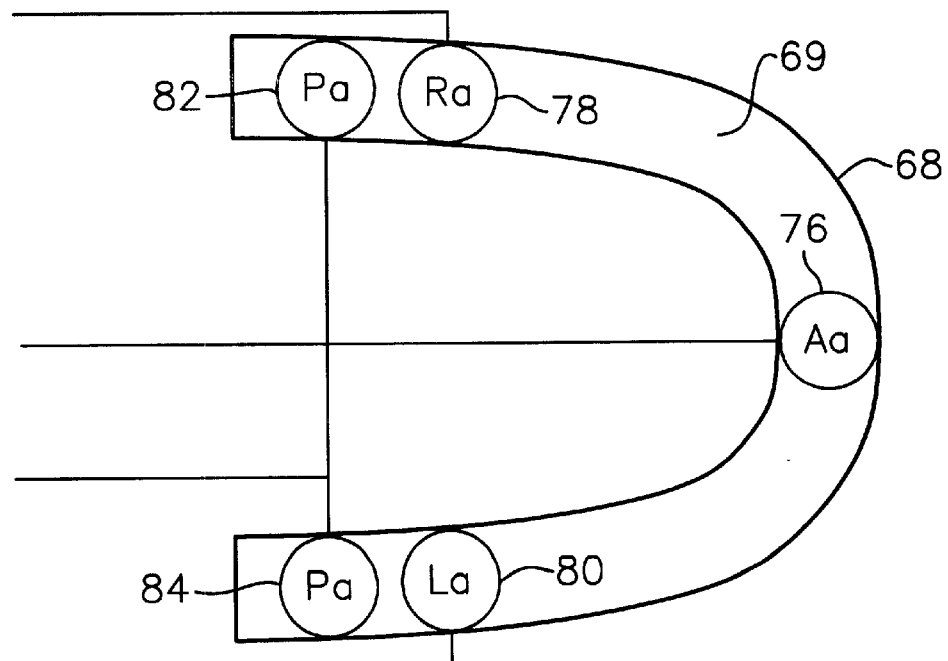
FIG. 6 is a bottom plan view of the mandibular splint portion of the intraoral device of this invention showing the gum side of the splint.
Figure 7:
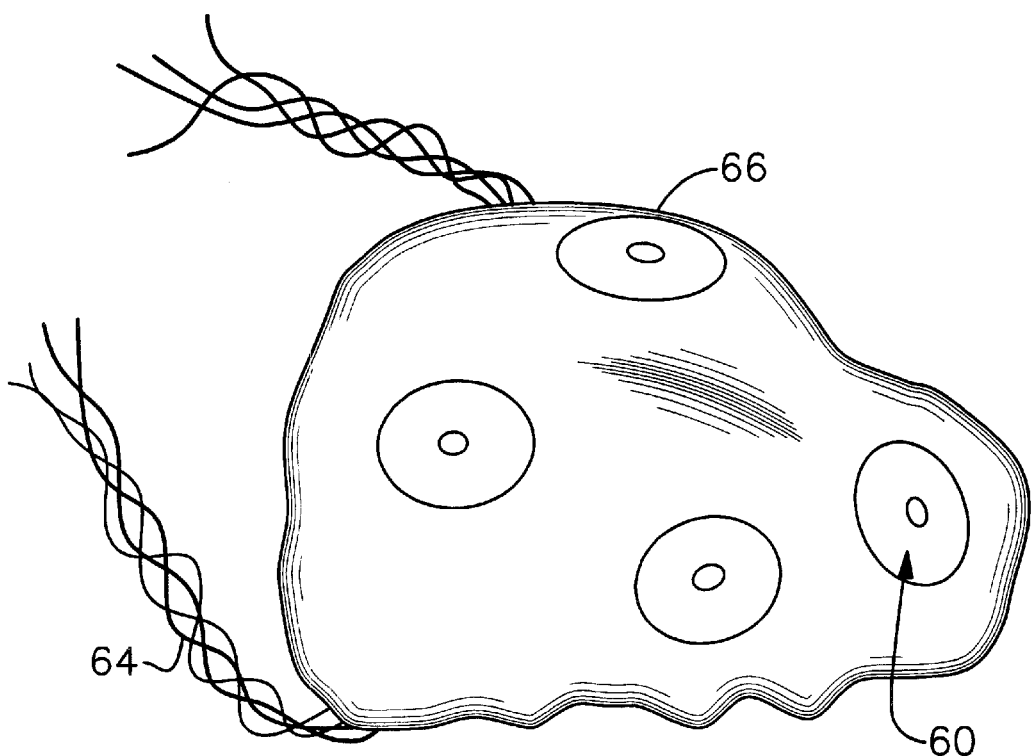
FIG. 7 is a perspective view of the device of FIG. 5.
Figure 8:
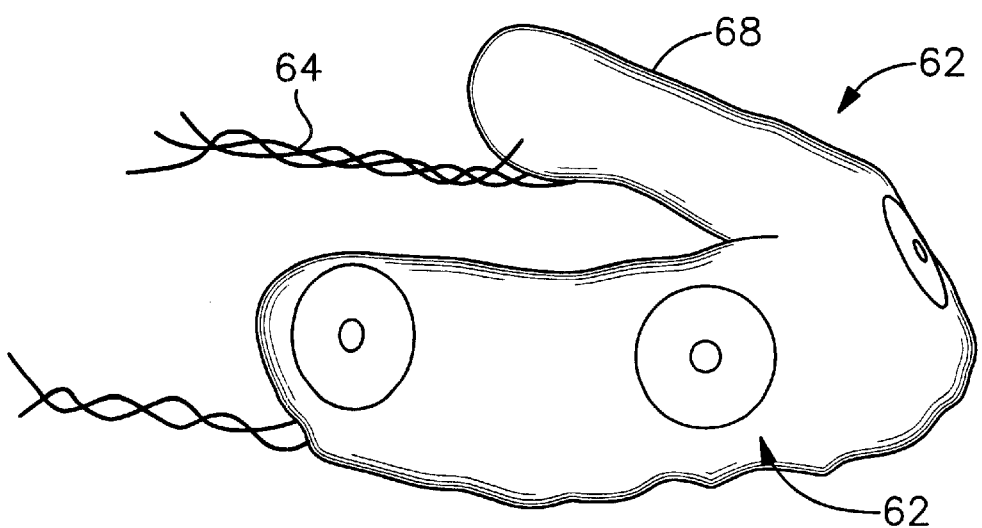
FIG. 8 is a perspective view of the device of FIG. 6.

An alternative to using an adaptive moving average process 28 having parallel processors is to us a compound moving average process, i.e., moving average processes in series, as illustrated in FIG. 4. The output of a moving average process is just the average of the data points in the process. Moving processes are inherently digital processes. Each data point of the moving average can represent a signal amplitude at a discrete time or the integral with respect to time of the signal amplitude between two discrete points in time. The output of a single moving average process, given a unit step input, varies linearly with time. A series of moving average processes 52-58, shown in FIG. 4, may be used in lieu of the parallel processes 32–40, shown in FIGS. 1(A–B) and 2, or in lieu of processor 40 to form a mixed adaptive compound moving average processor (MAMAPr). This modification will decrease response time. Each rectangle 52–58 represents a component of a compound moving average process with N points. The equivalent single moving average process would have 4N points. The output of each component, except for the last component, becomes the input for the next component. The effect of compounding is to retain the smoothing characteristics of the single, 4N point, moving average process while speeding up the maximum rate of change of the smoothed output. This is illustrated by comparing the four graphs in FIG. 20 with the single linear graph in FIG. 19.

Figure 19:
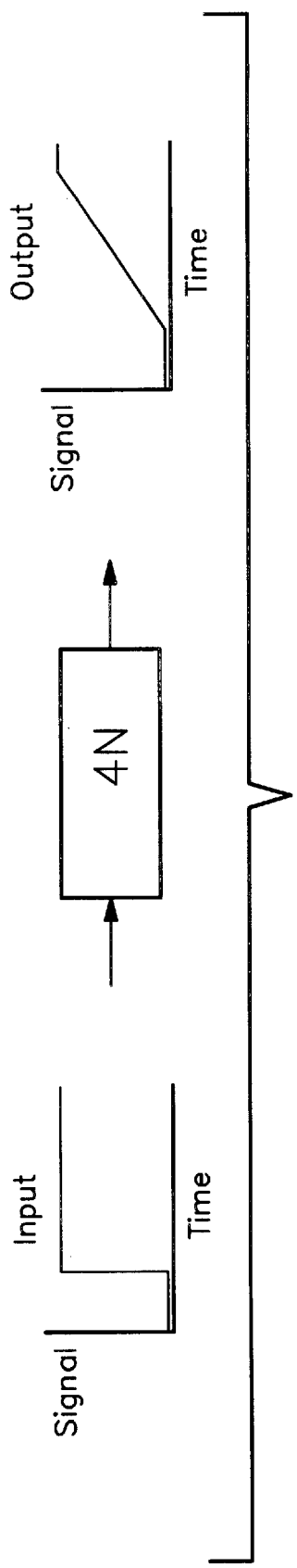
FIG. 19 shows a single moving average process with a graph of its input and output.
Figure 20:
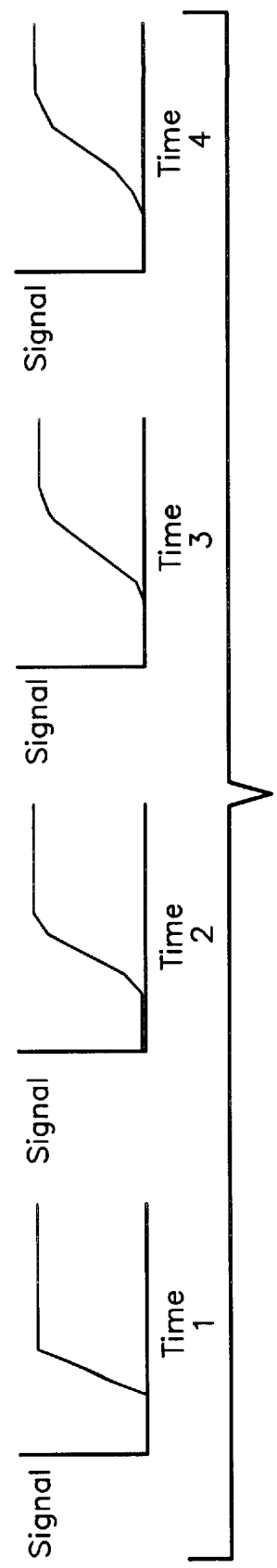
FIG. 20 shows four graphs of the output of each of the four moving average processes in series shown in FIG. 4.

The net effect of compounding is to reduce the time it takes to get to ninety percent of the final or maximum value following the input of a step function. As illustrated in FIG. 19, this value is reached after (0.9) (4n)(sampling interval) with a simple moving average process. FIG. 20 shows that the 90% point for a compound moving average process with four equal components is reached in approximately two thirds of this time or (0.6)(4N)(sampling time).

A mathematical description of a compound moving average process with four components of the same size (CMAPr) is set forth below.

Let A=the input value stream.
Then $$A^* = (1/N)\sum_{j=0}^{1-N} A_j$$

where N=the number of A values averaged. The current and previous N−1 values of A are averaged. A* is the output from the first component of the filter and the input to the second component.
Similarly, $$A^{*\prime} = (1/N)\sum_{j'=0}^{1-N} A^*{}_{j'}$$

is the output of the second component and, $$A^{*\prime\prime} = (1/N)\sum_{j''=0}^{1-N} A^{*\prime}{}_{j''}$$

is the output of the third component. Finally, the fourth, and last component's output is:

$$A^{*\prime\prime\prime} = (1/N)\sum_{j'''=0}^{1-N} A^{*\prime\prime}{}_{j'''}$$

where A*''' is the output of the compound moving average process (CMAPr).

The preferred intraoral device for detecting EMG signals from the tongue is illustrated in FIGS. 5–8. Electrode placement for the measurement of intraoral tongue electromyographic (EMG) signals is difficult due to 1) the proximity of the right, left, anterior and posterior tongue muscles in the oral cavity and 2) uncertainty concerning how and where to locate EMG signal recording electrodes in the mouth. Mandibular and maxillary splint electrode locations for measuring electromyographic signals from different areas of the tongue have been determined. Thin, stainless steel disc electrodes, generally indicated as 60 and 62, attached to fine Teflon-insulated multistrand wires 64 are imbedded onto the surface of mandibular 68 and maxillary 66 acrylic dental splints. Fine electrode wires run anteroposteriorly in the splint and exit distally around the last molar. After exiting the splints, the fine wires are braided into thin cables which continue anteriorly on each side within the buccal vestibule and exit the mouth at the right and left oral commissures. These electrode splint designs allow normal dental approximation, minimize interference with tongue movement and permit sealing of the lips to swallow saliva without drooling. These modified mandibular and maxillary splints can be used to evaluate unilateral or bilateral intraoral motor dysfunction, including dysphagia and dysarthria.

Mandibular and maxillary alginate impressions are taken using standard impression trays. Dental stone is poured into the impressions to form the mandibular and maxillary dental casts. Selection of electrode sites is made and locators of the EMG recording electrodes are drawn onto the dental casts with a pencil. A separating medium, such as Al-cote™ is brushed on the dental casts and allowed to dry.

For the measurement of EMG signals from the tongue, very fine multistrand Teflon-coated wires 64 (outer diameter of insulated wire is 0.53 mm) are attached to stainless steel disc electrodes 60 and 62 measuring approximately 1 cm in diameter and less than 0.5 mm in thickness. Prefabricated electrodes of this type are available from the Electrode Store, Buckley, Wash. The electrodes are placed on the gum side of the mandibular splint 68 and on the palate side 70 of the maxillary splint 66. The electrodes which are to lay adjacent to the mucosa of the gum under the tongue are placed facing the mandibular stone cast. Electrode wires are then oriented posteriorly, towards the second or third molars. Electrodes which are to lay adjacent to the mucosa of the hard palate are placed facing the maxillary stone cast or model with wires oriented posteriorly towards the last molar.

Orthodontic retainer acrylic is then applied using a standard "salt and pepper" technique. This acrylic application continues until electrodes at the desired locations are fixed in acrylic and the bases of the mandibular and maxillary splints are completed. Electrode wires are buried simultaneously with the electrodes within the acrylic as the mandibular and maxillary splint bases are built up.

Figure 9:
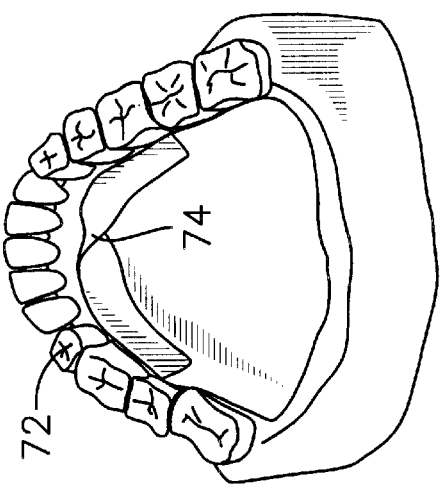
FIG. 9 is a perspective view of a dental mold having a fiberglass cloth inserted therein illustrating another aspect of this invention.

To improve mandibular 68 acrylic splint strength, a layer of light weight woven fiberglass material 72 (approximately 4–6 mm×40–50 mm in size and manufactured by Clark-Schwebel, Inc., Anderson, S.C.), as shown in FIG. 9, is incorporated into the anterior aspect of the splint. Lying within the acrylic, the woven fiberglass material 72 extends from the area of the mandibular splint adjacent to the right first molar to the area of the splint adjacent to the left first molar. A half twist 74, or 180° turn, is placed in the middle of the fiberglass cloth before the cloth is incorporated into the acrylic splint. The twist 74 in the fiberglass cloth is placed adjacent to the anterior aspect of the mandibular stone model. This prevents the fiberglass cloth from riding up too high along the middle to posterior aspect of the model as the cloth is incorporate into the acrylic splint.

All required electrodes are sequentially positioned onto the mandibular and maxillary splints with their wires oriented posteriorly and buried in the splint acrylic. The electrode wires emerge from the splints adjacent and posterior to the most distal tooth on each side of the mandibular or palatal arch. Electrode wires exiting each side of the splints are then braided into a cable to minimize size and to allow easy passage through the buccal vestibule and out the oral commissures. Braiding of the wires also prevents tangling of individual wires and decreases the risk of damage to individual wires during use of the splints. Electrode splints which use natural undercut retention can be difficult to remove from the dental stone models or casts. The acrylic splints can be easily cracked or otherwise damaged during the removal process. For this reason, the dental stone models containing the splints with electrodes are first thoroughly soaked in water in order to facilitate removing the acrylic splints from the models. Next, to avoid damage to the acrylic splints, the stone models are ground down around the splints on a model trimmer and the stone is carefully broken away from the splints.

The mandibular and maxillary splints are trimmed with a slow speed hand piece and acrylic bur.

If acrylic "flash" has hardened on the working surface of the electrodes, it must be carefully trimmed away to insure full electrode contact. Acrylic burs and rubber wheels can be utilized to create smooth surfaces to contact the intraoral mucosal tissues. The acrylic splints are washed with water and scrubbed with a toothbrush to remove any dental stone and separating medium remnants. Finally, the patient is examined wearing the special acrylic splints in order to assure proper fitting of the splints and acceptable patient comfort while wearing the splints.

EMG signal recording sites within the oral cavity are determined by where the active electrodes 76–84 are positioned. An active EMG electrode is placed as close to a motor end point (the area where the axons of a nerve sprout and join the muscle) as possible. To complete EMG signal measurement, reference recording electrodes 86–90 and a ground electrode 92 are needed. The reference EMG recording electrodes are customarily placed in a neutral area as far away as possible from the motor end points of the tongue muscle where there is less EMG signal.

Five active recording electrodes for measuring EMG activity of the tongue muscle are mounted equally spaced on the gum side 69 of the mandibular splint under the tongue muscle. Active right and left tongue muscle EMG recording electrodes are mounted onto the mid right 78 and left 80 gum side of the mandibular splint. The active anterior recording electrode 76 is placed anteriorly on the gum side of the mandibular splint 69. Two active EMG signal recording electrodes are placed on the right and left gum sides of the mandibular splint toward the posterior (pharyngeal) aspect of the splint. These two posterior electrodes 82 and 84 are jumpered together to form a posterior active electrode for the intraoral controller.

Two EMG signal reference electrodes for measuring EMG signals from the right and left tongue muscles are placed anteriorly on the right and left sides of the maxillary splint against the mucosa of the hard palate. The right active electrode on the mandibular splint used for measuring EMG signals from the muscles of the right tongue uses the reference electrode 90 against the right anterior hard palate. The active electrode used for measuring EMG signals from muscles of the left tongue uses the reference electrode 88 against the left anterior hard palate. A third single EMG signal reference electrode 86 is placed between the right and left reference electrodes on the hard palate side of the maxillary splint. This third reference electrode lies equidistant between the right and left edges of the splint along the midline of the anterior half of this splint. It is used as a common reference for the anterior and posterior active electrodes 76, 82 and 84 on the mandibular splint. A single ground electrode 92 is located approximately at the center of the maxillary splint against the mucosa of the hard palate.

EMG signals recorded from right, left, anterior and posterior electrode pairs (active and reference) can be combined after undergoing the EMG signal amplitude processing described above. A two-axis control signal can be formed by subtracting the myoelectric control signals from the right and left EMG signal recording electrode pairs (i.e., active and reference electrode pairs) and from the anterior and posterior EMG signal electrode pairs.

Powdered denture adhesives, such as Fasteeth™, when dissolved in water, have similar electrical impedances as conductive gels. These substances are used to cover the surfaces of the active and reference recording electrodes adjacent to the mucosa of the gums of the mandibular and to the mucosa of the hard palate in order to insure consistent electrical contact with the mucosa and low electrode impedances. The dental adhesive may also help to hold the maxillary splint against the hard palate.

EMG recording electrodes have been more precisely located using custom recording electrodes mounted onto the mandibular and maxillary splints. These newly designed electrodes have similar electrical properties as conventional electrodes, but are small enough to be imbedded in thin acrylic mandibular and maxillary splints. The small size of the surface electrodes and electrode cables allows the placement of at least five recording electrodes on a mandibular splint and at least four electrodes on the palate side of a maxillary splint.

The technique of running the fine wires of the electrodes antero-posteriorly in the splints to exit posteriorly around the last molar, of then passing the wires as a small braided cable through the buccal vestibule, and of finally having the braided cables exit the mouth through the oral commissures, allows the wearer normal dental approximation, minimizes interference with the wearer's normal tongue movement, and permits the wearer to seal their lips and to swallow saliva without drooling.

This technique for routing fine EMG electrode wires implanted in maxillary acrylic splints has been described previously for use with lingopalatal contacts on maxillary splints during dynamic palatography.

Placing 1 cm surface electrodes at multiple locations on the mandibular splint weakens the splint structurally. The use of fiberglass cloth strengthens the splint and prevents it from cracking and breaking, particularly around the anterior electrode where stresses are often greatest when putting in and taking out the splint.

The use of Fasteeth™ or other powdered denture adhesive as an electrode gel, decreases significantly the electronic noise recorded by the high impedance differential EMG input preamplifiers. Prior to the use of powdered dental adhesives as a conductive medium, conventional skin electrode gels were tried. They were found to be quite bitter and their noxious taste was not tolerated due to nausea and gagging.

From the foregoing description of the preferred embodiment of the invention, it will be apparent that many modifications may be made therein. It should be understood, however, that this embodiment of the invention is an exemplification of the invention only and that the invention is not limited thereto. It is to be understood, therefore, that it is intended in the appended claims to cover all modifications as fall within the true spirit and scope of the invention.

In addition to the above, the enclosed program used in the embodiment of this invention which refers to the adaptive moving average process, the exponential moving average process, and the windowing process is included below.

```
// ************************************************************************ // emgla.c
// Mark J Boyd
// 3-10-99
// ************************************************************************
//defines for dynamic variable width moving average filter #define w1 200
#define w2 300
#define w3 400
#define w4 500
#define w5 600
//defines that determine width dynamics
#define wsw 30 // signal change in period to start closing window
#define swo 30 // factor for rate of opening - larger is slower
#define swc 10 // factor for closing
#define swa 31 // factor for period length (31 ~ 100 ms) - must be odd!
// C includes files
#include "stdio.h"
#include "conio.h"
#include "stdlib.h"
#include "dos.h"
#include "time.h"
// Soundblaster routines
#include "sound.set"
// DAS-1600 driver includes files
#include "dasdecl.h"
#include "das1600.h"
// constant for exponential averaging
float alpha=.00313;
// Global variables, most for DAS functions
    DWORD      hDrv1600;            // Driver Handle
    DWORD      hDev1600;            // Device Handle
    DWORD      hFrameAD16001;       // A/D Frame Handle
    WORD far   *pDMABuf1;           // Pointer to allocated DMA buffer
    WORD       hMem1;               // allocated Memory Handle
    DWORD      hFrameAD16002;       // A/D Frame Handle
    WORD far   *pDMABuf2;           // Pointer to allocated DMA buffer
    WORD       hMem2;               // allocated Memory Handle
    short      nStatus;             // Used to monitor DMA transfers
    DWORD      dwTransfers;         // Used to monitor DMA transfers
    short      nErr;                // Function return error flag
    DWORD      dwSamples = 320;     // Number of samples to acquired
    char far   *szErrMsg;           // Pointer to error message
    clock_t    start,end;           // for timing
//Window edges:
int w[17] = {0,100,200,300,400,500,600,700,800,900,1000,1100,1200,1300, 1400,1500,200},wtmp;
//Storage for file data
int fdata[4] [1000], fdi=1000;
// function prototypes
void DisplayError(char *szFuncName, short nErr);
void InitDAS();
void winlist();
main()
{
//dummy variables for loops
register i,j,k=0;
int val1, val2, block, f, fn, fN, Win, Nsum, Ansum, div;
unsigned dummy, Blast, swflag=0;
```

-continued

```
// file variables
FILE *cfgfile;
// variables calculated during input cycle
// dummy's for use with keyboard instead of DASD
int v1=0,v2=0,v3=0,v4=0;
//matrix to hold last 1025 average reading in each channel,
//used for moving average filtering with width w[16]
int value[4] [1025] ={0}, trail;
// long sum variables accumulate sum of w[16] input values long sum1a=0
sum1b=0, sum1c=0,sum1d=0,sum1e=0,sum1f=0,sum1=0,oldsum1,oldsum2,oldsum3,oldsum4;
// for getch to test for /+window/-window/+width/-width/etc. char a;
// window output variables
int win1=1,
// sum variables divided by window width
nsum1,
// offsets for sum variables
n1=0,
// last window values
1win1=0,
// cursor value for display
cur1;
// exponential average history variables for nsums
float ansum1=0;
// Array holds width in w[16] for moving average
// and centers for windows in c[0],c[15] max is upper limit for window values int c[16],max=1600;
//read config file if it exists
cfgfile = fopen("emgla.cfg","r");
fscanf(cfgfile, "%5i", &w[16]);
for(i=1;i<16;i++) fscanf(cfgfile,"%5i",&w[i]);
fclose(cfgfile);
//Window centers are calculated from window edges
c[0] = w[1]/2;
for(i=1;i<15;i++) c[i]=(w[i]+w[i+1])/2;
c[15] = (w[15]+max)/2;
// Init DAS - this sets up two buffers and initialises the DAS for
// DMA transfer into those buffers
InitDAS();
clrscr();
// write slider scale
slider();
// This is a simple function to display the moving average width and the window // edges on the
top line of the screen
winlist();
// Write help info on bottom of screen
whelp();
// initialize sound system
isblaster();
// initially display channel 0
Win = win1;
Nsum = nsum1;
// Main loop
for (i=0;;i++)
{
if (kbhit())
// a long switch structure to handle single key commands
switch(getch())
{
case 'w';
{
.... lots of cases deleted
case 'q';
case 'Q';
    goto done;  // Stop dma on q/Q key press
}
// There are two buffers and two phases in this code to allow processing in one buffer whle DAM
//is filling the other buffer - this selects the even numbered phase
if(i/2*2 == i)
{
// Initiate acquisition in first buffer
    if ( ( ( nErr = K_DMAStart (hFrameAD16001) ) != 0)
    {
        DisplayError ("K_DMAStart", nErr);
        exit(1);
    }
if (i) // if not first pass do calcs on second buffer
{
// rectify and integrate values store in DMA buffer on last pass - note there are four
// independent data streams each of which gets the same processing
    for (j = 0; j < 80; j++)
```

-continued

```
        {
            value[0] [k] += abs((*(pDMABuf2+4*j)>>6) - 0x200);
        }
            value[0] [k] >>= 3;
// Do moving average filtering for five window widths
// with k as leading edge of window and trail as trailing edge
        trail = k - w1;
        if (trail < 0) trail = trail + 1025;
        sum1a = sum1a + value[0] [k] - value[0] [trail];
        trail = k - w2;
        if (trail < 0) trail = trail + 1025;
        sum1b = sum1b + value[0] [k] - value[0] [trail];
        trail = k - w3;
        if (trail < 0) trail = trail + 1025;
        sum1c = sum1c + value[0] [k] - value[0] [trail];
        trail = k - w4;
        if (trail < 0) trail = trail + 1025;
        sum1d = sum1d + value[0] [k] - value[0] [trail];
        trail = k - w5;
        if (trail < 0) trail = trail + 1025;
        sum1e = sum1e + valu[0] [k] - value[0] [trail];
        if (++k >= 1025) k =0; // circular queue
// now pick select window width based on value in w[16]
switch (w[16])
{
case w1:
{
        sum1 = sum1a;
}
break;
case w2:
{
        sum1 = sum1b;
}
break;
case w3:
{
        sum1 = sum1c;
}
break;
case w4:
{
        sum1 = sum1d;
}
break;
case w5:
{
        sum1 = sum1e;
}
}
        sum1f = sum1b/(w2/10);
// adjust sums for width and offset
nsum1 = sum1/w[16] - n1;
if (nsum1 < 0 ) nsum1 = 0;
// Calculate exponential average of nsums
ansum1 = (1-alpha)*ansum1 + alpha*nsum1;
// save old win values
1win1=win1;
// find possible new window value
win1 =0;
for(j=15;j>0;j--)
if(nsum1 > w[j])
{
win1=j;
break;
}
// Do not change the window if the new nsum value is not
// beyond the center of one of the windows adjacent to the
// current window - this allows rapid motion through many
// windows but prevents jumping back and forth between adjacent
// windows when the control value is jittering near the edge
if (win1 > 1win1 && nsum1 < c[1win1+1]) win1 = 1win1;
else if (win1 < 1win1 && nsum1 > c[1win1-1]) win1 = 1win1;
// But do change if the exponential average (weighting of alpha)
// of the nsum values has moved into another window. This allows
// slow motion between windows when nsum moves into and stays
// in a new window for about 1/(alpha) sample times. Do not do
// this change when the control signal is slewing (ansum - nsum >= 40)
// or if ansum and nsum are in different windows - nsum will always
```

-continued

```
// lead into a new window, but, if it got there rapidly, nsum may
// still be in the adjacent window and this will cause jitter if
// nsum drops into the half of the current window adjacent to the
// window occupied by the lagging ansum.
if (abs(ansum1-nsum1) < 40 && '((ansum1 > w[win1+1]) && (w[win1+1] > nsum1) || (nsum1 >
w[win1])\
&& (w[win1] > ansum1))) {
if (win1 <15 && ansum1 > w[win1+1]) win1 = win1+1;
else if (win1 >0 && ansum1 < w[win1]) win1 = win1-1;
}
Ansum = ansum1;
Win = win1;
Nsum = nsum1;
// pick octave in sound system
block=4; // choose block=4
if (Win>9) block++;
switch(Win)
{
case 0;
fn=577;
break;
. . . long switch to select frequency
case 15;
fn=686;
break;
}
// calc freq for tone coloring
if(Win<15)
    fN=3*(float) (Nsum · w[Win])/(w[Win+1]-w[Win]);
else
    fN=3*(float) (Nsum · w[Win])/(max-w[Win]);
switch((int)fN)
{
case 0;
fN=fn*.98;
break;
case 1:
fN=fn;
break;
case 2:
fN=fn*1.05;
break;
}
if(!(Blast == 1))
{
// do tones
    fm(0xA0,(fn & 0xFF));
    fm(0xA1,(fN & 0xFF));
    fm(0xB0, ((fn >> 8) & 0x3) + (block <<2) | KEYON);
    fm(0xB1,((fN >> 8) & 0x3) + (block << 2) | KEYON);
}
// Display cursor showing position in window
window(1,11,80,12);
clrscr();
disp_cursor();
// Display data about control channels in a window near the top of // the screen
if(i/10*10==i) (
window(10,5,50,9);
clrscr();
disp_data()
}
// Wait for DMA to end
    do
    {
        K_DMAStatus(hFrameAD16001, &nStatus, &dwTransfers);   ] while (nStatus & 1);
}
else
{
// Initiate acquisition in second buffer
    if ( ( nErr = K_DMAStart (hFrameAD16002) ) '= 0)
    {
        DisplayError("K_DMAStart", nErr);
        exit(1);
    }
// Do calcs on first buffer
. . . essentially a repeat of the processing for the first buffer.
}
// write data to file if z command is active
// note the use of the phase number for timing. Each phase is a fixed interval determined by the
```

-continued

```
// DMA settings. I/div*div**I is only true when I is a multiple of div.
if((fdi < 1000)&&(i/div*div**i))
{
...
}
// similar timing logic is used to pace the widening and narrowing of the adaptive moving average
// filter
if (i/swa*swa**i) //100 ms
{
if(abs(oldsum1-sum1f) > wsw)
{
swflag = 0;
}
else
{
swflag++
}
//swflag is used as a flag and as a phase counter
if (!swflag)
{
// narrowing of adaptive moving average filter
if (swflag/swc*swc**swflag)
    switch (w[16])
        {
        base w5: w[16] = w4;
        break;
        case w4: w[16] = w3;
        break;
        case w3: w[16] = w2;
        break;
        case w2: w[16] '2 w1;
        }
}
else
// widening of adaptive moving average filter
if (swflag/swo*swo**swflag)
    switch (w[16])
        {
        case w1: w[16] '2 w2;
        break;
        case w2: w[16] = w3;
        break;
        case w3: w[16] = w4;
        break;
        case w4: w[16] = w5;
        }
}
window(1,1,80,2);
clrscr();
disp_widths()
oldsum1=sum1f;
}
#ifdef DAS
// Wait for DMA to end
        do
        [
            K_DMAStatus(hFrameAD16002, &nStatus, &dwTransfers);   } while (nStatus & 1);
#endif
}
#ifdef DAS
// Check status 2nd bit for overrun
        if (nStatus & 2)
            printf("Overrun error during DMA transfer\n");
#endif
}
done:
//clean up and exit code
...
}
```

What is claimed is:

1. An intraoral device for detecting EMG signals from the tongue comprising:

a splint having at least one electrode attached thereto; said splint being made of acrylic;

woven fiberglass imbedded in the acrylic for increasing the strength of the splint.

2. A intraoral device as set forth in claim 1, wherein said splint has anterior and posterior regions; said fiberglass being received primarily in said anterior region of said splint.

3. A intraoral device as set forth in claim 1, wherein said fiberglass is in the form of a cloth; said cloth having a twist therein near the middle of the cloth, thereby preventing the cloth from riding too high while the splint is being manufactured.

* * * * *